(12) United States Patent
Leung

(10) Patent No.: US 6,503,700 B1
(45) Date of Patent: *Jan. 7, 2003

(54) MAMMALIAN CDP-DIACYLGLYCEROL SYNTHASE

(75) Inventor: David W. Leung, Mercer Island, WA (US)

(73) Assignee: Cell Therapeutics, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/282,218

(22) Filed: Mar. 31, 1999

(51) Int. Cl.[7] .................................................. C12N 9/12
(52) U.S. Cl. ............................ 435/4; 435/183; 435/194; 536/23.2
(58) Field of Search ............................ 435/4, 183, 194; 536/23.2

(56) References Cited

U.S. PATENT DOCUMENTS 5,952,480 A * 9/1999 Leung et al. ............... 536/23.2

OTHER PUBLICATIONS

M. Volta, et al., "Identification and Characterization of CDS2, a Mammalian Homolog of the Drosophila CDP–diacylglycerol Synthase Gene," pp. 68–77, Genomics vol. 55 (1999).
Homo sapiens mRNA for CDS2 protein, EMBL Accesssion No. Y16521 (1999).
Athanasios Lykidis, et al., "The Role of CDP–Diacylglycerol Synthetase and Phosphatidylinositol Synthase Activity Levels in the Regulation of Cellular Phosphatidylinositol Content," pp. 33402–33409, The Journal of Biological Chemistry, vol. 272, No. 52, (1997).

Stephanie Halford, et al., "Short Communication—Isolation and Chromosomal Localization of Two Human CDP–diacylglycerol Synthase (CDS) Genes," pp. 140–144, Genomics vol. 54, No. 1 (1998).

Reitha Weeks, et al., "Isolation and Expression of an Isoform of Human CDP–Diacylglycerol Synthase cDNA," pp. 281–289, DNA and Cell Biology, vol. 16, No. 3 (1997).

DNASIS for Windows Version 2.5, DNA and Protein Sequence Analysis System, Reference Manual, pp. 123–131 (1997).

CDP–diacylglycerol synthase 2, NCBI Accession No. 3892191 (1998).

Anne M. Heacock, et al., "Rapid Communication—Cloning of CDP–Diacylglycerol Synthase from a Human Neuronal Cell Line," pp. 2200–2203, Journal of Neurochemistry, vol. 67, No. 5, (1996).

* cited by examiner

*Primary Examiner*—Rebecca E. Prouty
*Assistant Examiner*—David J. Steadman
(74) *Attorney, Agent, or Firm*—Foley & Lardner

(57) ABSTRACT

There is disclosed cDNA sequences and polypeptides having the enzyme CDP-diacylglycerol synthase (CDS) activity. CDS is also known as CTP:phosphatidate cytidylyltransferase. There is further disclosed methods for isolation and production of polypeptides involved in phosphatidic acid metabolism and signaling in mammalian cells, in particular, the production of purified forms of CDS.

7 Claims, 23 Drawing Sheets

FIG. 1A

```
           10          20          30          40          50          60
TCTATGGTGG GGCCGCGTTA GTGGCTGCGG CTCCGCGGGA CTCCAGGGCG CGGCTGCGAG
           70          80          90         100         110         120
GTGGCGGGGC GCCCCGCCTG CAGAACCCTG CTTGCAGCTC AGGTTTCGGG GTGCTTGAGG
          130         140         150         160         170         180
AGGCCGCCAC GGCAGCGGCG GAGCGGAAGA TGTTGGAGCT GAGGCACCGG GGAAGCTGCC
          190         200         210         220         230         240
CCGGCCCCAG GGAAGCGGTG TCGCCCGCCAC ACCGCGAGGG AGAGGCGGCC GGCGGGCGACC
          250         260         270         280         290         300
ACGAAACCGA GAGCACCAGC GACAAAGAAA CAGATATTGA TGACAGATAT GGAGATTTGG
          310         320         330         340         350         360
ATTCCAGAAC AGATTCTGAT ATTCCGGAAA TTCCACCATC CTCAGATAGA ACCCCTGAGA
          370         380         390         400         410         420
TTCTCAAAAA AGCTCTATCT GGTTTATCTT CAAGGTGGAA AAACTGGTGG ATACGTGGAA
```

FIG. 1B

```
         430        440        450        460        470        480
TTCTCACTCT AACTATGATC TCGTTGTTTT TCCTGATCAT CTATATGGGA TCCTTCATGC 490        500        510        520        530        540
TGATGCTTCT TGTTCTGGGC ATCCAAGTGA AATGCTTCCA TGAAATTATC ACTATAGTT
550        560        570        580        590        600
ATAGAGTCTA TCATTCTTAT GATCTACCAT GGTTTAGAAC ACTAAGTTGG TACTTTCTAT 610        620        630        640        650        660
TGTGTGTAAA CTACTTTTTC TATGGAGAGA CTGTAGCTGA TTATTTTGCT ACATTTGTTC 670        680        690        700        710        720
AAAGAGAAGA ACAACTTCAG TTCCCTCATTC GCTACCATAG ATTTATATCA TTTGCCCTCT 730        740        750        760        770        780
ATCTGGCAGG TTTCTGCATG TTTGTACTGA GTTTGGTGAA GGAACATTAT CGTCTGCAGT 790        800        810        820        830        840
TTTATATGTT CGCATGGACT CATGTCACTT TACTGATAAC TGTCACTCAG TCACACCTTG
850        860        870        880        890        900
```

FIG. 1C

```
TCATCCAAAAA TCTGTTTGAA GGCATGATAT GGTTCCTTGT TCCAATATCA AGTGTTATCT
   910         920         930        940         950        960
GCAATGACAT AACTGCTTAC CTTTTTTGGAT TTTTTTTTGG GAGAACTCCA TTAATTAAGT
   970         980         990        1000        1010       1020
TGTCTCCTAA AAAGACTTGG GAAGGATTCA TTGGTGGTTT CTTTTCCACA GTTGTGTTTG
   1030        1040        1050       1060        1070       1080
GATTCATTGC TGCCTATGTG TTATCCAAAT ACCAGTACTT TGTCTGCCCA GTGGAATACC
   1090        1100        1110       1120        1130       1140
GAAGTGATGT AAACTCCTTC GTGACAGAAT GTGAGCCCTC AGAACTTTTC CAGCTTCAGA
   1150        1160        1170       1180        1190       1200
CTTACTCACT TCCACCCTTT CTAAAGGCAG TCTTGAGACA GGAAAGAGTG AGCTTGTACC
   1210        1220        1230       1240        1250       1260
CTTTCCAGAT CCACAGCATT GCACTGTCAA CCTTTGCATC TTTAATTGGC CCATTTGGAG
   1270        1280        1290       1300        1310       1320
```

FIG. 1D

```
GCTTCTTTGC TAGTGGATTC AAAAGAGCCT TCAAAATCAA GGATTTGCA AATACCATTC
        1330       1340       1350       1360       1370       1380
CTGGACATGG TGGGATAATG GACAGATTTG ATTGTCAGTA TTTGATGGCA ACTTTTGTAC
        1390       1400       1410       1420       1430       1440
ATGTGTACAT CACAAGTTTT ATAAGGGGCC CAAATCCCAG CAAAGTGCTA CAGCAGTTGT
        1450       1460       1470       1480       1490       1500
TGGTGCTTCA ACCTGAACAG CAGTTAAATA TATATAAAAC CCTGAAGACT CATCTCATTG
        1510       1520       1530       1540       1550       1560
AGAAAGGAAT CCTACAACCC ACCTTGAAGG TATAACTGGA TCCAGAGAGG GAAGGACTGA
        1570       1580       1590       1600       1610       1620
CAAGAAGGAA TTATTCAGAA AAACACTGAC AGATGTTTTA TAAATTGTAC AGAAAAATAG
        1630       1640       1650       1660       1670       1680
TTAAAAATGC AATAGGTTGA AGTTTTGGAG ATATGTTTCT CTCTGAAATT ACTGTGAATA
        1690       1700       1710       1720       1730       1740
```

FIG. 1E

```
TTTAACAAAC ACTTACTTGA TCTATGTTAT GAAATAAGTA GCAAATTGCC AGCAAAATGT
                1750       1760       1770       1780       1790       1800
CTTGTACCTT TTCTAAAGTG TATTTTCTGA TGTGAACTTC CTTCCCCTTA CTTGCTAGGT
                1810       1820       1830       1840       1850       1860
TTCATAATTT AAAAGACTGG TATTAAAAAG AGTCAAACAC TATAAAAATGA GTAAGTTGAC
                1870       1880       1890       1900       1910       1920
GATGTTTTAA GATTGCACCT GGCAGTGTGC CTTTTTGCAC AAATATTTAC TTTTGCACTT
                1930       1940       1950       1960       1970       1980
GGAGCTGCTT TTAATTTTAG CAAAAATGTTT TATGCAAGGC ACAATAGGAA GTCAGTTCTC
                1990       2000       2010       2020       2030       2040
CTGCACTTCC TCCTCATGTA GTCTGGAGTA CTTTCTAAAG GGCTTAGTTG GATTTAAAAA
                2050       2060       2070       2080       2090       2100
AAAAAAAAAA AGGGGGGCCG CTCTAGAGGA TCCCTCGAGG GGCCCAAGCT TACGCGTGCA
                2110       2120       2130       2140       2150       2160
```

TGC..........................................

```
  1  TCTATGGTGGGGCCGCGTTAGTGGCTGCGCGGGACTCCAGGGGCGGCTGCGAGGT         62
 63  GGCGGGGCGGCCCCGGCCCTGCAGAACCCTGCTTGCAGCTTCAGTTTCGGGGTGCTTGAGGAG  122

123  GCCGCCACGGCAGCGCGGGAGCGGAAG ATG TTG GAG CTG AGG CAC CGG GGA     173
  1                              Met Leu Glu Leu Arg His Arg Gly       8

174  AGC TGC CCC GGC CCC AGG GAA GCG GTG TCG CCG CCA CAC CGC GAG     218
  8  Ser Cys Pro Gly Pro Arg Glu Ala Val Ser Pro Pro His Arg Glu     23

219  GGA GAG GCG GCC GGC GAC CAC GAA ACC GAG AGC ACC GAC             263
 23  Gly Glu Ala Ala Gly Asp His Glu Thr Glu Ser Thr Asp             38

264  AAA GAA ACA GAT ATT GAT GAC AGA TAT GGA GAT TTG GAT TCC AGA     308
 38  Lys Glu Thr Asp Ile Asp Asp Arg Tyr Gly Asp Leu Asp Ser Arg     53

309  ACA GAT TCT GAT ATT CCG GAA ATT CCA CCA TCC TCA GAT AGA ACC     353
 53  Thr Asp Ser Asp Ile Pro Glu Ile Pro Pro Ser Ser Asp Arg Thr     68

354  CCT GAG ATT CTC AAA AAA GCT CTA TCT GGT TTA TCT TCA AGG TGG     398
 68  Pro Glu Ile Leu Lys Lys Ala Leu Ser Gly Leu Ser Ser Arg Trp     83

399  AAA AAC TGG TGG ATA CGT GGA ATT CTC ACT CTA ACT ATG ATC TCG     443
 83  Lys Asn Trp Trp Ile Arg Gly Ile Leu Thr Leu Thr Met Ile Ser     98
```

FIG. 2B

| | | | | | | | | | |
|---|---|---|---|---|---|---|---|---|---|
| 444 | TTG | TTT | TTC | CTG | ATC | TAT | ATG | GGA | TCC | TTC | ATG | CTG | ATG | CTT | 488 |
| 98 | Leu | Phe | Phe | Leu | Ile | Tyr | Met | Gly | Ser | Phe | Met | Leu | Met | Leu | 113 |

| 489 | CTT | GTT | CTG | GGC | ATC | CAA | GTG | AAA | TGC | TTC | CAT | GAA | ATT | ATC | ACT | 533 |
| 113 | Leu | Val | Leu | Gly | Ile | Gln | Val | Lys | Cys | Phe | His | Glu | Ile | Ile | Thr | 128 |

| 534 | ATA | GGT | TAT | AGA | GTC | TAT | CAT | TCT | TAT | GAT | CTA | CCA | TGG | TTT | AGA | 578 |
| 128 | Ile | Gly | Tyr | Arg | Val | Tyr | His | Ser | Tyr | Asp | Leu | Pro | Trp | Phe | Arg | 143 |

| 579 | ACA | CTA | AGT | TGG | TAC | TTT | CTA | TTG | TGT | GTA | AAC | TAC | TTT | TTC | TAT | 623 |
| 143 | Thr | Leu | Ser | Trp | Tyr | Phe | Leu | Leu | Cys | Val | Asn | Tyr | Phe | Phe | Tyr | 158 |

| 624 | GGA | GAG | ACT | GTA | GCT | GAT | TAT | TTT | GCT | ACA | TTT | GTT | CAA | AGA | GAA | 668 |
| 158 | Gly | Glu | Thr | Val | Ala | Asp | Tyr | Phe | Ala | Thr | Phe | Val | Gln | Arg | Glu | 173 |

| 669 | GAA | CAA | CTT | CAG | TTC | CTC | ATT | CGC | TAC | CAT | AGA | TTT | ATA | TCA | TTT | 713 |
| 173 | Glu | Gln | Leu | Gln | Phe | Leu | Ile | Arg | Tyr | His | Arg | Phe | Ile | Ser | Phe | 188 |

| 714 | GCC | CTC | TAT | CTG | GCA | GGT | TTC | TGC | ATG | TTT | GTA | CTG | AGT | TTG | GTG | 758 |
| 188 | Ala | Leu | Tyr | Leu | Ala | Gly | Phe | Cys | Met | Phe | Val | Leu | Ser | Leu | Val | 203 |

| 759 | AAG | GAA | CAT | TAT | CGT | CTG | CAG | TTT | TAT | ATG | TTC | GCA | TGG | ACT | CAT | 803 |
| 203 | Lys | Glu | His | Tyr | Arg | Leu | Gln | Phe | Tyr | Met | Phe | Ala | Trp | Thr | His | 218 |

FIG. 2C

```
 804 GTC ACT TTA CTG ATA ACT GTC ACT CAG TCA CAC CTT GTC ATC CAA  848
 218 Val Thr Leu Leu Ile Thr Val Thr Gln Ser His Leu Val Ile Gln  233

849 AAT CTG TTT GAA GGC ATG ATA TGG TTC CTT GTT CCA ATA TCA AGT  893
 233 Asn Leu Phe Glu Gly Met Ile Trp Phe Leu Val Pro Ile Ser Ser  248

894 GTT ATC TGC AAT GAC ATA ACT GCT TAC CTT TTT GGA TTT TTT TTT  938
 248 Val Ile Cys Asn Asp Ile Thr Ala Tyr Leu Phe Gly Phe Phe Phe  263

939 GGG AGA ACT CCA TTA ATT AAG TTG TCT CCT AAA AAG ACT TGG GAA  983
 263 Gly Arg Thr Pro Leu Ile Lys Leu Ser Pro Lys Lys Thr Trp Glu  278

984 GGA TTC ATT GGT GGT TTC TTT TCC ACA GTT GTG TTT GGA TTC ATT 1028
 278 Gly Phe Ile Gly Gly Phe Phe Ser Thr Val Val Phe Gly Phe Ile  293

1029 GCT GCC TAT GTG TTA TCC AAA TAC CAG TAC TTT GTC TGC CCA GTG 1073
 293 Ala Ala Tyr Val Leu Ser Lys Tyr Gln Tyr Phe Val Cys Pro Val  308

1074 GAA TAC CGA AGT GAT GTA AAC TCC TTC GTG ACA GAA TGT GAG CCC 1118
 308 Glu Tyr Arg Ser Asp Val Asn Ser Phe Val Thr Glu Cys Glu Pro  323

1119 TCA GAA CTT TTC CAG CTT CAG ACT TAC TCA CTT CCA CCC TTT CTA 1163
 323 Ser Glu Leu Phe Gln Leu Gln Thr Tyr Ser Leu Pro Pro Phe Leu  338

1164 AAG GCA GTC TTG AGA CAG GAA AGA GTG AGC TTG TAC CCT TTC CAG 1208
```

FIG. 2D

```
 338 Lys Ala Val Leu Arg Gln Glu Arg Val Ser Leu Tyr Pro Phe Gln   353

1209 ATC CAC AGC ATT GCA CTG TCA ACC TTT GCA TCT TTA ATT GGC CCA  1253
 353 Ile His Ser Ile Ala Leu Ser Thr Phe Ala Ser Leu Ile Gly Pro   368

1254 TTT GGA GGC TTC TTT GCT AGT GGA TTC AAA AGA GCC TTC AAA ATC  1298
 368 Phe Gly Gly Phe Phe Ala Ser Gly Phe Lys Arg Ala Phe Lys Ile   383

1299 AAG GAT TTT GCA AAT ACC ATT CCT GGA CAT GGT GGG ATA ATG GAC  1343
 383 Lys Asp Phe Ala Asn Thr Ile Pro Gly His Gly Gly Ile Met Asp   398

1344 AGA TTT GAT TGT CAG TAT TTG ATG GCA ACT TTT GTA CAT GTG TAC  1388
 398 Arg Phe Asp Cys Gln Tyr Leu Met Ala Thr Phe Val His Val Tyr   413

1389 ATC ACA AGT TTT ATA AGG GGC CCA AAT CCC AGC AAA GTG CTA CAG  1433
 413 Ile Thr Ser Phe Ile Arg Gly Pro Asn Pro Ser Lys Val Leu Gln   428

1434 CAG TTG TTG GTG CTT CAA CAG CAG TTA AAT ATA TAT AAA           1478
 428 Gln Leu Leu Val Leu Gln Gln Gln Leu Asn Ile Tyr Lys           443

1479 ACC CTG AAG ACT CAT CTC ATT GAG AAA GGA ATC CTA CAA CCC ACC  1523
 443 Thr Leu Lys Thr His Leu Ile Glu Lys Gly Ile Leu Gln Pro Thr   458

1524 TTG AAG GTA TAA CTGGATCCAGAGAGGGAAGGACTGACAAGAAGGAATTATTCAGA 1579
 458 Leu Lys Val ***                                                462
```

FIG. 2E

```
1580 AAAACACTGACAGATGTTTATAAATTGTACAGAAAAATAGTTAAAAATGCAATAGGTTG  1639
1640 AAGTTTGGAGATATGTTTCTCTCTGAAATTACTGTGAATATTAACAAACACTTACTTG    1699
1700 ATCTATGTTATGAAATAGCAAATTGCCAGCAAATGTCTTGTACCTTTCTAAAGT        1759
1760 GTATTTCTGATGTGAACTTCCCTCCCCCTTACTTGCTAGGTTTCATAATTTAAAAGACTG  1819
1820 GTATTTAAAAGAGTCAAACACTATAAAATGAGTAAGTTGACGATGTTTAAGATTGCACC   1879
1880 TGGCAGTGTGCCTTTTTGCACAAATATTTACTTTTGCACTTGGAGCTGCTTTTAATTTTA  1939
1940 GCAAAATGTTTATGCAAGGCACAATAGGAAGTCAGTTCCTCCTGCACTTCCTCCCTCATGT 1999
2000 AGTCTGGAGTACTTTCTAAAGGGCTTAGTTGGATTTAAAAAAAAAAAAAAA           2050
```

FIG. 3A

| | | | | | | |
|---|---|---|---|---|---|---|
| | | | Met Leu Glu Leu Arg His Arg Gly | 8 |
| Ser Cys Pro Gly Pro Arg Glu Ala Val Ser Pro Pro His Arg Glu | 23 |
| Gly Glu Ala Ala Gly Gly Asp His Glu Thr Glu Ser Thr Ser Asp | 38 |
| Lys Glu Thr Asp Ile Asp Asp Arg Tyr Gly Asp Leu Asp Ser Arg | 53 |
| Thr Asp Ser Asp Ile Pro Glu Ile Pro Pro Ser Ser Asp Arg Thr | 68 |
| Pro Glu Ile Leu Lys Lys Ala Leu Ser Gly Leu Ser Ser Arg Trp | 83 |
| Lys Asn Trp Trp Ile Arg Gly Ile Leu Thr Leu Thr Met Ile Ser | 98 |
| Leu Phe Phe Leu Ile Ile Tyr Met Gly Ser Phe Met Leu Met Leu | 113 |
| Leu Val Leu Gly Ile Gln Val Lys Cys Phe His Glu Ile Ile Thr | 128 |
| Ile Gly Tyr Arg Val Tyr His Ser Tyr Asp Leu Pro Trp Phe Arg | 143 |
| Thr Leu Ser Trp Tyr Phe Leu Leu Cys Val Asn Tyr Phe Phe Tyr | 158 |

FIG. 3B

| | |
|---|---|
| Gly Glu Thr Val Ala Asp Tyr Phe Ala Thr Phe Val Gln Arg Glu | 173 |
| Glu Gln Leu Gln Phe Leu Ile Arg Tyr His Arg Phe Ile Ser Phe | 188 |
| Ala Leu Tyr Leu Ala Gly Phe Cys Met Phe Val Leu Ser Leu Val | 203 |
| Lys Glu His Tyr Arg Leu Gln Phe Tyr Met Phe Ala Trp Thr His | 218 |
| Val Thr Leu Leu Ile Thr Val Thr Gln Ser His Leu Val Ile Gln | 233 |
| Asn Leu Phe Glu Gly Met Ile Trp Phe Leu Val Pro Ile Ser Ser | 248 |
| Val Ile Cys Asn Asp Ile Thr Ala Tyr Leu Phe Gly Phe Phe Phe | 263 |
| Gly Arg Thr Pro Leu Ile Lys Leu Ser Pro Lys Lys Thr Trp Glu | 278 |
| Gly Phe Ile Gly Gly Phe Phe Ser Thr Val Val Phe Gly Phe Ile | 293 |
| Ala Ala Tyr Val Leu Ser Lys Tyr Gln Tyr Phe Val Cys Pro Val | 308 |
| Glu Tyr Arg Ser Asp Val Asn Ser Phe Val Thr Glu Cys Glu Pro | 323 |
| Ser Glu Leu Phe Gln Leu Gln Thr Tyr Ser Leu Pro Pro Phe Leu | 338 |

FIG. 3C

| | |
|---|---|
| Lys Ala Val Leu Arg Gln Glu Arg Val Ser Leu Tyr Pro Phe Gln | 353 |
| Ile His Ser Ile Ala Leu Ser Thr Phe Ala Ser Leu Ile Gly Pro | 368 |
| Phe Gly Gly Phe Phe Ala Ser Gly Phe Lys Arg Ala Phe Lys Ile | 383 |
| Lys Asp Phe Ala Asn Thr Ile Pro Gly His Gly Gly Ile Met Asp | 398 |
| Arg Phe Asp Cys Gln Tyr Leu Met Ala Thr Phe Val His Val Tyr | 413 |
| Ile Thr Ser Phe Ile Arg Gly Pro Asn Pro Ser Lys Val Leu Gln | 428 |
| Gln Leu Leu Val Leu Gln Pro Glu Gln Leu Asn Ile Tyr Lys | 443 |
| Thr Leu Lys Thr His Leu Ile Glu Lys Gly Ile Leu Gln Pro Thr | 458 |
| Leu Lys Val *** | 461 |

FIG. 4

```
                         10         20         30         40         50
Human        1 MLELRHRGSC PGPREAVSPP HREGEAAGGD HETESTSDKE TDIDDRYGDL
Drosophila   1 MAEVRRR--- KGEDEPLEDT AISGSDAANK RNSAADSSDH VDSEEEKIPE
Yeast        1 MSD------- ---------- ----NPEMKP HGIS-KEIVE SVTDATSKAI
E. coli      1 MLAAWEW--- ---------- ---------- ---------- ----------
                         60         70         80         90        100
Human       51 DSRTDSDIPE IPPSSDRTPE ILKKALSGLS SRWKNWWIRG ILI--LTMIS
Drosophila  51 EKFVDELAKN LPQGTDKTPE ILDSALKDLP DRWKNWVIRG IFTW--IMIC
Yeast       51 DKLQEELHKD ASESV--TPV TKESTAATKE SRKYNFFIRT V--WTFVMIS
E. coli     51 ----GQLS-- ---------- ---------- ----GFTTRS QRVW-LAVLC
                        110        120        130        140        150
Human      101 LFFLIIYMGS FMLMLLVLGI QVKCFHEIIT IGYRVYHSYD LPWFRTLSWY
Drosophila 101 GFALIIYGGP LALMITTLLV QVKCFQEIIS IGYQVYRIHG LPWFRSLSWY
Yeast      101 GFFITLASGH AWCIVLILGC QIATFKECIA VTSASGREKN LPLTKTLNWY
E. coli    101 GLLLAL---- -------MLF LLPEYHRNIH QP-----LVE ISLWASLGWW
                        160        170        180        190        200
Human      151 FLLCV--NYF FYGETVADYF ATFVQREEQL QFLIRYHRFI SFALYLAGFC
Drosophila 151 FLL--TSNYF FYGENLVDYF GVVINRVEYL KFLVTYHRFL SFALYIIGFV
Yeast      151 LLF--TTIYY LDGKSLFKFE QATFYEYPVL NFIVTNHKFI CYCLYLMGFV
E. coli    151 IVALLLVLFY PGSAAIWR-- -----NSKTL RLIFG----- --VLTIVPFF
                        210        220        230        240        250
Human      201 MFVLSLVKEH YRLQFYMFAW THVTLLITVT QSHLVIQNLF EGMIWFLVPI
Drosophila 201 WFVLSLVKKY YIKQFSLFAW THVSLLIVVT QSYLIIQNIF EGLIWFIYPV
Yeast      201 LFVCSLRKGF LKFQFGSLCV THMVLLLVVF QAHLIIKNVL NGLFWFLLPC
E. coli    201 WGMLALRA-- --WHYD---- ---------- ------ENHY SGAIWLLYVM
                        260        270        280        290        300
Human      251 SSVICNDITA YLFGFFFGRT PLI-KLSPKK TWEGFIGGFF STVVFGFIAA
Drosophila 251 SMIVCNDVMA YVFGFFFGRT PLI-KLSPKK TWEGFIGGGF ATVLFGILFS
Yeast      251 GLVIVNDIFA YLCGITFGKT KLIE-ISPKK TLEGFLGAWE FIALASIILT
E. coli    251 ILVWGADSGA YMFGKLFGKH KLAPKVSPGK TWQGFIGG-- -------LAT
                        310        320        330        340        350
Human      301 YVLSKYQYFV CPVEYRSDVN SFVTECEPSE LFQLQTYSLP PFLKAVLRQE
Drosophila 301 YVLCNYQYFI CPIQYSEEQG RMTMSCVPSY LFTPQEYSLK LFGIG----K
Yeast      301 RILSPYTYLT CPVEDLHTNF FSNLTCELNP VFLPQVYRLP PIFFDKVQIN
E. coli    301 AAVISWGYGM ---------- ---------- ---------- ---WANLDVA
                        360        370        380        390
Human      351 RVSLYPFQIH SIALSTFASL IGPFGGFFAS GFKRAFKIKD FANTIPGHGG
Drosophila 351 TLNLYPFIWH SISLSLFSSI IGPFGGFFAS GFKRAFKIKD FGDMIPGHGG
Yeast      351 SITVKPIYFH ALNLATFASL FAPFGGFFAS GLKRTFKVKD FGHSIPGHGG
E. coli    351 PVTL------ -LICSIVAAL ASVLGDLTES MFKREAGIKD SGHLIPGHGG
                        410        420        430        440        450
Human      401 IMDRFDCQYL MATLVHGYIT SFI---RGPN PSKVLQQLLV LQPEQQLNIY
Drosophila 401 IMDRFDCQFL MATFVNVY-- --ISFIRTPS PAKLLTQIYN LKPD------
Yeast      401 ITDRVDCQFI MGSFANLYYE TFISEHRITV DTVLSTILMN LNDKQIIELI
E. coli    401 ILDRIDS--- ---------- -------LTA AVPVFACLLL L---------
                        460        470        480        490        500
Human      451 KTLKTHLIEK GI-------- LQPTLKV--- ---------- ..........
Drosophila 451 ---------- --QQYQIYQS -------LKD NLGHMLT... ..........
Yeast      451 DILIRFLSKK GIISAKNFEK LADIFNVTKK SLTNHS*... ..........
E. coli    451 ---------- ---------- ---VFRTL*- ---------- ..........
```

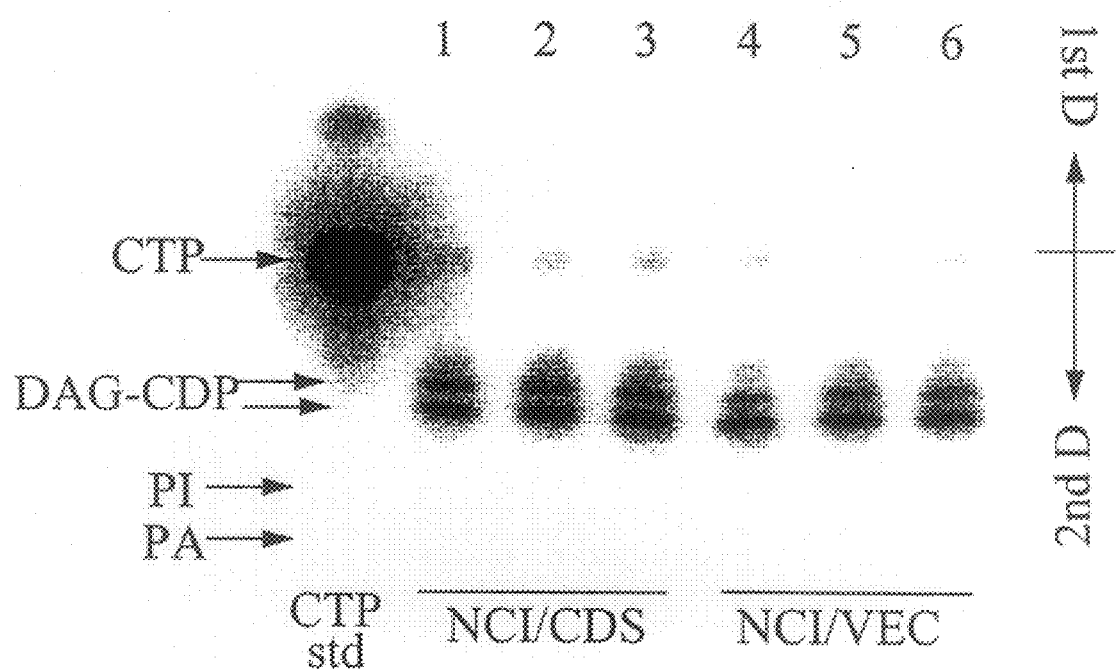

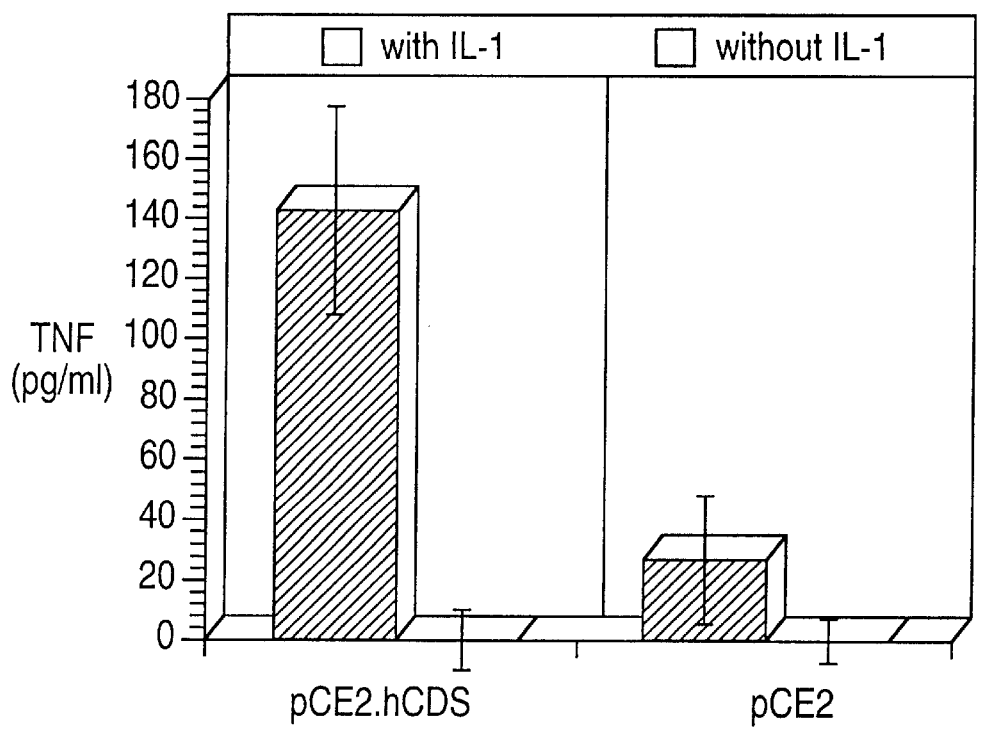
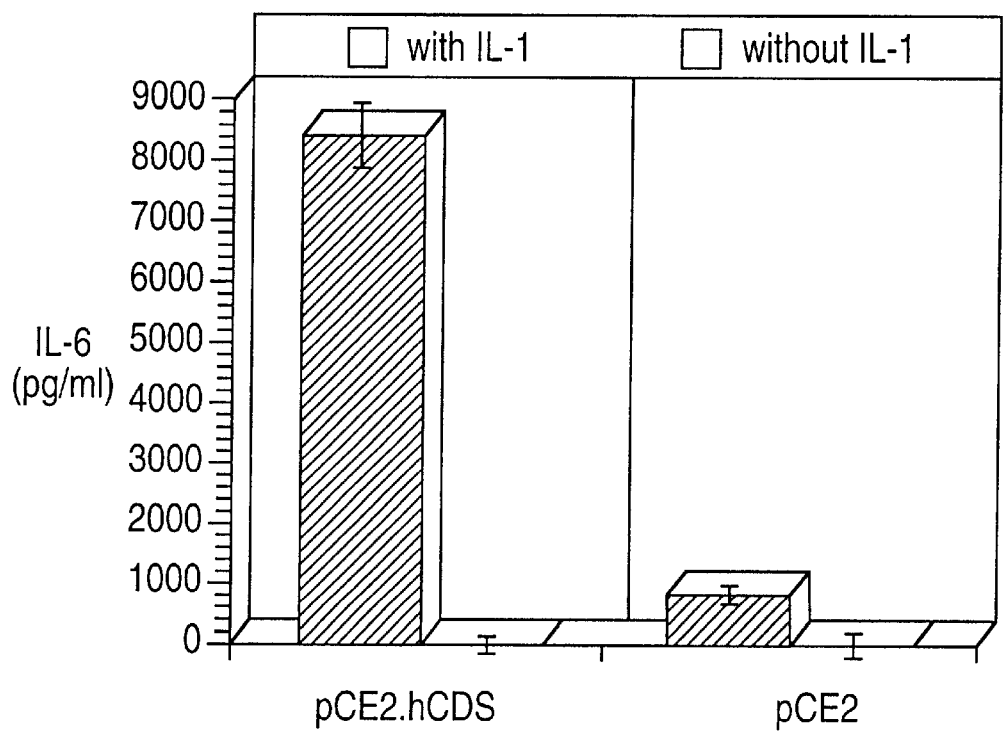

FIG. 8A  Translated sequence of human CDP-DAG Synthase-2 (hCDS-2)

```
CGACGTCGGGCCGATTTTCCCAGG ATG ACA GAG CTG AGG CAG AGG GTG GCC         51
                         Met Thr Glu Leu Arg Gln Arg Val Ala
                                           5
CAT GAG CCG GTT GCG CCA CCC GAG GAC AAG GAG TCA GAG TCA GAA          96
His Glu Pro Val Ala Pro Pro Glu Asp Lys Glu Ser Glu Ser Glu
10              15                  20
GCA AAG GTA GAT GGA GAG ACT GCA TCG GAC AGT GAG AGC CAG GCA         141
Ala Lys Val Asp Gly Glu Thr Ala Ser Asp Ser Glu Ser Gln Ala
25              30                  35
GAA TCC GCA CCC CTG CCA GTC TCT GCA GAT GAT ACC CCG GAG GTC         186
Glu Ser Ala Pro Leu Pro Val Ser Ala Asp Asp Thr Pro Glu Val
40              45                  50
CTC AAT AGG GCC CTT TCC AAC TTG TCT TCA AGA TGG AAG GAC TGG         231
Leu Asn Arg Ala Leu Ser Asn Leu Ser Ser Arg Trp Lys Asp Trp
55              60                  65
TGG GTG AGA GGC ATC CTG ACT TTG GCC ATG ATT GCA TTT TTC TTC         276
Trp Val Arg Gly Ile Leu Thr Leu Ala Met Ile Ala Phe Phe Phe
70              75                  80
ATC ATC ATT TAC CTG GGA CCA ATG GTT TTG ATG ATA ATC GTG ATG         321
Ile Ile Ile Tyr Leu Gly Pro Met Val Leu Met Ile Ile Val Met
85              90                  95
TGC GTT CAG ATT AAG TGT TTC CAT GAG ATA ATC ACT ATT GGC TAC         366
Cys Val Gln Ile Lys Cys Phe His Glu Ile Ile Thr Ile Gly Tyr
100             105                 110
AAC GTC TAC CAC TCA TAT GAT CTG CCC TGG TTC AGG ACG CTC AGC         411
Asn Val Tyr His Ser Tyr Asp Leu Pro Trp Phe Arg Thr Leu Ser
115             120                 125
TGG TAC TTT CTC CTG TGT GTA AAC TAT TTC TTC TAT GGT GAG ACA         456
Trp Tyr Phe Leu Leu Cys Val Asn Tyr Phe Phe Tyr Gly Glu Thr
130             135                 140
GTG ACG GAT TAC TTC TTC ACC CTG GTC CAG AGA GAA GAG CCT TTG         501
Val Thr Asp Tyr Phe Phe Thr Leu Val Gln Arg Glu Glu Pro Leu
145             150                 155
CGG ATT CTC AGT AAA TAC CAC CGG TTC ATT TCC TTT ACT CTC TAT         546
Arg Ile Leu Ser Lys Tyr His Arg Phe Ile Ser Phe Thr Leu Tyr
160             165                 170
CTA ATA GGA TTC TGC ATG TTT GTA CTG AGT CTG GTC AAG AAG CAT         591
Leu Ile Gly Phe Cys Met Phe Val Leu Ser Leu Val Lys Lys His
175             180                 185
TAT CGA CTG CAG TTC TAC ATG TTT GGC TGG ACC CAT GTG ACA TTG         636
Tyr Arg Leu Gln Phe Tyr Met Phe Gly Trp Thr His Val Thr Leu
190             195                 200
CTG ATT GTT GTA ACA CAG TCA CAT CTT GTT ATC CAC AAC CTA TTT         681
Leu Ile Val Val Thr Gln Ser His Leu Val Ile His Asn Leu Phe
205             210                 215
GAA GGA ATG ATC TGG TTC ATT GTC CCC ATA TCT TGT GTG ATC TGT         726
Glu Gly Met Ile Trp Phe Ile Val Pro Ile Ser Cys Val Ile Cys
220             225                 230
AAT GAC ATC ATG GCC TAT ATG TTT GGC TTT TTC TTT GGT CGG ACC         771
Asn Asp Ile Met Ala Tyr Met Phe Gly Phe Phe Phe Gly Arg Thr
235             240                 245
CCA CTC ATC AAG CTG TCC CCG AAG AAG ACC TGG GAA GGC TTC ATT         816
Pro Leu Ile Lys Leu Ser Pro Lys Lys Thr Trp Glu Gly Phe Ile
250             255                 260
GGG GGC TTC TTT GCT ACT GTG GTG TTT GGC CTT CTG CTG TCC TAT         861
Gly Gly Phe Phe Ala Thr Val Val Phe Gly Leu Leu Leu Ser Tyr
265             270                 275
GTG ATG TCC GGG TAC AGA TGC TTT GTC TGC CCT GTG GAG TAC AAC         906
Val Met Ser Gly Tyr Arg Cys Phe Val Cys Pro Val Glu Tyr Asn
280             285                 290
AAT GAC ACC AAC AGC TTC ACT GTG GAC TGT GAG CCC TCG GAC CTG         951
Asn Asp Thr Asn Ser Phe Thr Val Asp Cys Glu Pro Ser Asp Leu
295             300                 305
TTT CGC CTG CAG GAG TAC AAC ATT CCT GGG GTG ATC CAG TCA GTC         996
```

FIG. 8B

```
    Phe Arg Leu Gln Glu Tyr Asn Ile Pro Gly Val Ile Gln Ser Val
    310                     315                 320
    ATT GGC TGG AAA ACG GTC CGG ATG TAC CCC TTC CAG ATT CAC AGC      1041
    Ile Gly Trp Lys Thr Val Arg Met Tyr Pro Phe Gln Ile His Ser
    325                     330                 335
    ATC GCT CTC TCC ACC TTT GCC TCG CTC ATT GGC CCC TTT GGA GGA      1086
    Ile Ala Leu Ser Thr Phe Ala Ser Leu Ile Gly Pro Phe Gly Gly
    340                     345                 350
    TTC TTC GCA AGT GGA TTC AAA CGA GCC TTT AAA ATC AAA GAC TTT      1131
    Phe Phe Ala Ser Gly Phe Lys Arg Ala Phe Lys Ile Lys Asp Phe
    355                     360                 365
    GCC AAT ACC ATT CCT GGC CAT GGA GGC ATC ATG GAT CGC TTT GAC      1176
    Ala Asn Thr Ile Pro Gly His Gly Gly Ile Met Asp Arg Phe Asp
    370                     375                 380
    TGC CAG TAT CTG ATG GCC ACC TTT GTC AAT GTA TAC ATC GCC AGT      1221
    Cys Gln Tyr Leu Met Ala Thr Phe Val Asn Val Tyr Ile Ala Ser
    385                     390                 395
    TTT ATC AGA GGC CCT AAC CCA AGC AAA CTG ATT CAG CAG TTC CTG      1266
    Phe Ile Arg Gly Pro Asn Pro Ser Lys Leu Ile Gln Gln Phe Leu
    400                     405                 410
    ACT TTA CGG CCA GAT CAG CAG CTC CAC ATC TTC AAC ACG CTG CGG      1311
    Thr Leu Arg Pro Asp Gln Gln Leu His Ile Phe Asn Thr Leu Arg
    415                     420                 425
    TCT CAT CTG ATC GAC AAA GGG ATG CTG ACA TCC ACC ACA GAG GAC      1356
    Ser His Leu Ile Asp Lys Gly Met Leu Thr Ser Thr Thr Glu Asp
    430                     435                 440
    GAG TAG GGGCCACCCAGGGCCAGGAGAACAGGAACAGAACTGAGCAGGGGCAGGTCT      1413
    Glu ***
    445
    CCAAGGCAAGCCCAGCTGGTGTGACTTAGACAATGACGAGGCTTCAACTCACTGTCTTTT    1473
    TTTTTTTTTTTTTTTGGAGGGTATTTTTTATTTGTGGGTTCAAAAAATCTGTATATACA    1533
    GTCTATGTGTTTAGAATTTGTGTTGTAAGTAAACTACAGCTTTGAGTTGGAAAGAAGTCA    1593
    CGGGTTGTAAAACCATTTGGATTTTTTAAAACAAAAGTATTAATAATCTGGAAGACAGT    1653
    GTTGCCCAGGTCAGGAGTGTTTTCTTGGTGGTTCCAGCCCCCATCAATTGAACTGTTTCT    1713
    GGGCTCAGTCAGACACAGACATTCATCTGTGTCTGACCAAATCAGGGGACTTCCCCACCT    1773
    GTGGTGGGAGGCACAGCTTAGATGTTTTGTACACCTGGTCTTTTCTAGAAATCCCTGCTT    1833
    GGAGCTGCAGAAGGGTTGCCTTCTGTAGGTCGGAGGAATGGAGGCTTACTAACCAGGTAA    1893
    GCCTTCTATGCATCCACACCAAAATCCTGCAGAATGTAAGTAAGCTCTGCTTTATAAGAT    1953
    GGGTTCACCTTCATCGCAGACTGAAAGTTTCAGTTTTATTTTTTCAGAAAGCACGAAA     2013
    AATTATTTATAATAGTCTGGAGAAAAAACACACTGTAATATTTCAAGTGTATGCAGTAGA    2073
    ATGTACTGTAACTGAGCCCTTTCCCACATGTCTAGGCTCCAATGTCTCCTGTAGGTCCAC    2133
    CTAACTGTGTGTTTTCAGGGACAATGCCATCCATGTTTGTGCTGTAGACTTGCTGCTGCT    2193
    GAATCCTTTCTGGGGACTTTCTCATCGGGCAGGGAGCAGAGGGCTTCTCGTTCATGCACC    2253
    CTTTGCCTGAACACCCATGTAGCTGCTGTGTTGTGTATATATTACTCTTAAGAGGAGTGT    2313
    GTGTGTCTGTGTTTGTTTTAAAAGTCACTTATTTCTTACAGTGATTTCAATTGCACCATG    2373
    ACTTCTTCACTAAAACCACAAAGTCCTGCTTAAAACTATGGAAAACCTAACCTGATTAGA    2433
    GCCTTGACTATTTTGAAGATTAAATGCACACTTTTTATATAAAAAAAAAAAAAA         2488
```

FIG. 9

Homology of human CDS2 and CDS1 protein sequences.

```
                 10         20         30         40         50
H_CDS2   MTELRQRVA- ---HEPVAPE EDKESESEAK VDGETASDSE SQ--------
H_CDS1   MLERHRGSC PGPREAVSPP HREGEAAGGD HETESTSDKE TDIDDRYGDL
                 60         70         80         90        100

H_CDS2   ------AESAP LRVSADDTPE VLNRALSNLS SRWKDWVRG ILTLAMIAFE
H_CDS1   DSRTDSDIPE IPPSSDRTPE ILKKALSGLS SRWKNWWIRG ILTLTMISLF
                110        120        130        140        150

H_CDS2   FIIIYLGPMV LMIIVMCVQI KCFHELITIG YNVYHSYDLP WERTISWYFL
H_CDS1   FLIIYMGSFM LMLLVLGIQV KCFHELILIG YRVYHSYDLP WERTISWYFL
                160        170        180        190        200

H_CDS2   LCVNYFFYGE TVTDYEFTLV QREEPLRILS KYHREISETL YLIGECMEVL
H_CDS1   LGVNYFEYGE TVADYEAIFV QREEQLQFLI RYHREISFAL YLIAGECMEVL
                210        220        230        240        250

H_CDS2   SLVKKHYRLQ FYMEGWTHVT LLIIVTQSHL VIHNLFEGMI WEIVPISCVI
H_CDS1   SLVKKHYRLQ FYMEAWTHVT LLILVTQSHL VIQNLFEGMI WELVEISSVI
                260        270        280        290        300

H_CDS2   CNDIMAYMFG FEEGRTPLIK LSPKKTWEGE IGGFFATVVF GLLLSYVMSG
H_CDS1   CNDITAYLFG FEEGRTPLIK LSPKKTWEGF IGGEFSTVVF GFIAAYVLSK
                310        320        330        340        350

H_CDS2   YRCFVCPVEY NNDTNSETVD CEPSDLERLQ GEFASGEKRA VIGWKTVRMY
H_CDS1   YQFVCPVEY RSDVNSEVTE CEPSELEQLQ GEFASGEKRA VLRQERVSLY
                360        370        380        390        400

H_CDS2   PEQIHSIALS TEASLIGPEG FKIKDFANTI PGHGGIMDRE
H_CDS1   PEQIHSIALS TEASLIGPEG FKIKDFANTI PGHGGIMDRF
                410        420        430        440        450

H_CDS2   NVYIASEIRG PNPSKLIQQF LTLRPDQQLH IFNTLRSHLI
H_CDS1   HVYITSEIRG PNPSKVLQQL LVLQPEQQLN IYKTLKTHLI
                460

H_CDS2   DKGMLTSTTE DE*
H_CDS1   EKGILQPTLK V*
```

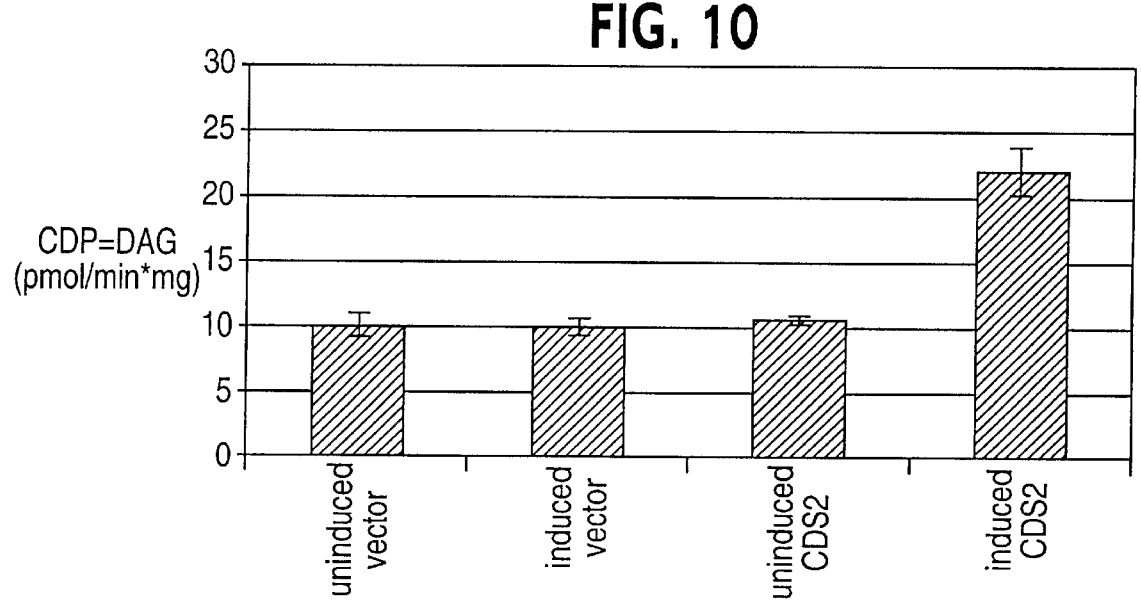

RT-PCR of matched cancer vs normal prostate tissues c = cancer
n = normal
g = genomic DNA
(-) = no cDNA

SEQUENCE LISTING

<160> NUMBER OF SEQ ID NOS: 19

<210> SEQ ID NO 1
<211> LENGTH: 2051
<212> TYPE: DNA
<213> ORGANISM: Homo sapiens
<220> FEATURE:
<221> NAME/KEY: CDS
<222> LOCATION: (150)..(1532)

<400> SEQUENCE: 1

```
tctatggtgg ggccgcgtta gtggctgcgg ctccgcggga ctccagggcg cggctgcgag      60
gtggcggggc gccccgcctg cagaaccctg cttgcagctc aggtttcggg gtgcttgagg     120
aggccgccac ggcagcgcgg gagcggaag atg ttg gag ctg agg cac cgg gga       173
                                 Met Leu Glu Leu Arg His Arg Gly
                                   1               5 agc tgc ccc ggc ccc agg gaa gcg gtg tcg ccg cca cac cgc gag gga       221
Ser Cys Pro Gly Pro Arg Glu Ala Val Ser Pro Pro His Arg Glu Gly
    10                  15                  20 gag gcg gcc ggc ggc gac cac gaa acc gag agc acc agc gac aaa gaa       269
Glu Ala Ala Gly Gly Asp His Glu Thr Glu Ser Thr Ser Asp Lys Glu
 25                  30                  35                  40 aca gat att gat gac aga tat gga gat ttg gat tcc aga aca gat tct       317
Thr Asp Ile Asp Asp Arg Tyr Gly Asp Leu Asp Ser Arg Thr Asp Ser
                45                  50                  55 gat att ccg gaa att cca cca tcc tca gat aga acc cct gag att ctc       365
Asp Ile Pro Glu Ile Pro Pro Ser Ser Asp Arg Thr Pro Glu Ile Leu
            60                  65                  70 aaa aaa gct cta tct ggt tta tct tca agg tgg aaa aac tgg tgg ata       413
Lys Lys Ala Leu Ser Gly Leu Ser Ser Arg Trp Lys Asn Trp Trp Ile
        75                  80                  85 cgt gga att ctc act cta act atg atc tcg ttg ttt ttc ctg atc atc       461
Arg Gly Ile Leu Thr Leu Thr Met Ile Ser Leu Phe Phe Leu Ile Ile
    90                  95                 100 tat atg gga tcc ttc atg ctg atg ctt ctt gtt ctg ggc atc caa gtg       509
Tyr Met Gly Ser Phe Met Leu Met Leu Leu Val Leu Gly Ile Gln Val
105                 110                 115                 120 aaa tgc ttc cat gaa att atc act ata ggt tat aga gtc tat cat tct       557
Lys Cys Phe His Glu Ile Ile Thr Ile Gly Tyr Arg Val Tyr His Ser
                125                 130                 135 tat gat cta cca tgg ttt aga aca cta agt tgg tac ttt cta ttg tgt       605
Tyr Asp Leu Pro Trp Phe Arg Thr Leu Ser Trp Tyr Phe Leu Leu Cys
            140                 145                 150 gta aac tac ttt tat gga gag act gta gct gat tat ttt gct aca           653
Val Asn Tyr Phe Phe Tyr Gly Glu Thr Val Ala Asp Tyr Phe Ala Thr
        155                 160                 165 ttt gtt caa aga gaa gaa caa ctt cag ttc ctc att cgc tac cat aga       701
Phe Val Gln Arg Glu Glu Gln Leu Gln Phe Leu Ile Arg Tyr His Arg
    170                 175                 180
```

```
ttt ata tca ttt gcc ctc tat ctg gca ggt ttc tgc atg ttt gta ctg     749
Phe Ile Ser Phe Ala Leu Tyr Leu Ala Gly Phe Cys Met Phe Val Leu
185                 190                 195                 200 agt ttg gtg aag gaa cat tat cgt ctg cag ttt tat atg ttc gca tgg     797
Ser Leu Val Lys Glu His Tyr Arg Leu Gln Phe Tyr Met Phe Ala Trp
                205                 210                 215 act cat gtc act tta ctg ata act gtc act cag tca cac ctt gtc atc     845
Thr His Val Thr Leu Leu Ile Thr Val Thr Gln Ser His Leu Val Ile
            220                 225                 230 caa aat ctg ttt gaa ggc atg ata tgg ttc ctt gtt cca ata tca agt     893
Gln Asn Leu Phe Glu Gly Met Ile Trp Phe Leu Val Pro Ile Ser Ser
        235                 240                 245 gtt atc tgc aat gac ata act gct tac ctt ttt gga ttt ttt ttt ggg     941
Val Ile Cys Asn Asp Ile Thr Ala Tyr Leu Phe Gly Phe Phe Phe Gly
    250                 255                 260 aga act cca tta att aag ttg tct cct aaa aag act tgg gaa gga ttc     989
Arg Thr Pro Leu Ile Lys Leu Ser Pro Lys Lys Thr Trp Glu Gly Phe
265                 270                 275                 280 att ggt ggt ttc ttt tcc aca gtt gtg ttt gga ttc att gct gcc tat    1037
Ile Gly Gly Phe Phe Ser Thr Val Val Phe Gly Phe Ile Ala Ala Tyr
                285                 290                 295 gtg tta tcc aaa tac cag tac ttt gtc tgc cca gtg gaa tac cga agt    1085
Val Leu Ser Lys Tyr Gln Tyr Phe Val Cys Pro Val Glu Tyr Arg Ser
            300                 305                 310 gat gta aac tcc ttc gtg aca gaa tgt gag ccc tca gaa ctt ttc cag    1133
Asp Val Asn Ser Phe Val Thr Glu Cys Glu Pro Ser Glu Leu Phe Gln
        315                 320                 325 ctt cag act tac tca ctt cca ccc ttt cta aag gca gtc ttg aga cag    1181
Leu Gln Thr Tyr Ser Leu Pro Pro Phe Leu Lys Ala Val Leu Arg Gln
    330                 335                 340 gaa aga gtg agc ttg tac cct ttc cag atc cac agc att gca ctg tca    1229
Glu Arg Val Ser Leu Tyr Pro Phe Gln Ile His Ser Ile Ala Leu Ser
345                 350                 355                 360 acc ttt gca tct tta att ggc cca ttt gga ggc ttc ttt gct agt gga    1277
Thr Phe Ala Ser Leu Ile Gly Pro Phe Gly Gly Phe Phe Ala Ser Gly
                365                 370                 375 ttc aaa aga gcc ttc aaa atc aag gat ttt gca aat acc att cct gga    1325
Phe Lys Arg Ala Phe Lys Ile Lys Asp Phe Ala Asn Thr Ile Pro Gly
            380                 385                 390 cat ggt ggg ata atg gac aga ttt gat tgt cag tat ttg atg gca act    1373
His Gly Gly Ile Met Asp Arg Phe Asp Cys Gln Tyr Leu Met Ala Thr
        395                 400                 405 ttt gta cat gtg tac atc aca agt ttt ata agg ggc cca aat ccc agc    1421
Phe Val His Val Tyr Ile Thr Ser Phe Ile Arg Gly Pro Asn Pro Ser
    410                 415                 420 aaa gtg cta cag cag ttg ttg gtg ctt caa cct gaa cag cag tta aat    1469
Lys Val Leu Gln Gln Leu Leu Val Leu Gln Pro Glu Gln Gln Leu Asn
425                 430                 435                 440 ata tat aaa acc ctg aag act cat ctc att gag aaa gga atc cta caa    1517
Ile Tyr Lys Thr Leu Lys Thr His Leu Ile Glu Lys Gly Ile Leu Gln
                445                 450                 455 ccc acc ttg aag gta taactggatc cagagaggga aggactgaca agaaggaatt    1572
Pro Thr Leu Lys Val
            460 attcagaaaa acactgacag atgttttata aattgtacag aaaaatagtt aaaaatgcaa    1632 taggttgaag ttttggagat atgtttctct ctgaaattac tgtgaatatt taacaaacac    1692 ttacttgatc tatgttatga aataagtagc aaattgccag caaaatgtct tgtacctttt    1752 ctaaagtgta ttttctgatg tgaacttcct tcccttact tgctaggttt cataatttaa     1812
```

-continued

```
aagactggta tttaaaagag tcaaacacta taaaatgagt aagttgacga tgttttaaga   1872
ttgcacctgg cagtgtgcct ttttgcacaa atatttactt ttgcacttgg agctgctttt   1932
aattttagca aaatgtttta tgcaaggcac aataggaagt cagttctcct gcacttcctc   1992
ctcatgtagt ctggagtact ttctaaaggg cttagttgga tttaaaaaaa aaaaaaaaa    2051
```

<210> SEQ ID NO 2
<211> LENGTH: 461
<212> TYPE: PRT
<213> ORGANISM: Homo sapiens

<400> SEQUENCE: 2

```
Met Leu Glu Leu Arg His Arg Gly Ser Cys Pro Gly Pro Arg Glu Ala
 1               5                  10                  15

Val Ser Pro Pro His Arg Glu Gly Ala Ala Gly Gly Asp His Glu
                20                  25                  30

Thr Glu Ser Thr Ser Asp Lys Glu Thr Asp Ile Asp Asp Arg Tyr Gly
            35                  40                  45

Asp Leu Asp Ser Arg Thr Asp Ser Asp Ile Pro Glu Ile Pro Pro Ser
        50                  55                  60

Ser Asp Arg Thr Pro Glu Ile Leu Lys Lys Ala Leu Ser Gly Leu Ser
    65                  70                  75                  80

Ser Arg Trp Lys Asn Trp Trp Ile Arg Gly Ile Leu Thr Leu Thr Met
                85                  90                  95

Ile Ser Leu Phe Phe Leu Ile Ile Tyr Met Gly Ser Phe Met Leu Met
               100                 105                 110

Leu Leu Val Leu Gly Ile Gln Val Lys Cys Phe His Glu Ile Ile Thr
           115                 120                 125

Ile Gly Tyr Arg Val Tyr His Ser Tyr Asp Leu Pro Trp Phe Arg Thr
       130                 135                 140

Leu Ser Trp Tyr Phe Leu Leu Cys Val Asn Tyr Phe Phe Tyr Gly Glu
145                 150                 155                 160

Thr Val Ala Asp Tyr Phe Ala Thr Phe Val Gln Arg Glu Glu Gln Leu
                165                 170                 175

Gln Phe Leu Ile Arg Tyr His Arg Phe Ile Ser Phe Ala Leu Tyr Leu
            180                 185                 190

Ala Gly Phe Cys Met Phe Val Leu Ser Leu Val Lys Glu His Tyr Arg
        195                 200                 205

Leu Gln Phe Tyr Met Phe Ala Trp Thr His Val Thr Leu Leu Ile Thr
    210                 215                 220

Val Thr Gln Ser His Leu Val Ile Gln Asn Leu Phe Glu Gly Met Ile
225                 230                 235                 240

Trp Phe Leu Val Pro Ile Ser Ser Val Ile Cys Asn Asp Ile Thr Ala
                245                 250                 255

Tyr Leu Phe Gly Phe Phe Gly Arg Thr Pro Leu Ile Lys Leu Ser
            260                 265                 270

Pro Lys Lys Thr Trp Glu Gly Phe Ile Gly Gly Phe Phe Ser Thr Val
        275                 280                 285

Val Phe Gly Phe Ile Ala Ala Tyr Val Leu Ser Lys Tyr Gln Tyr Phe
    290                 295                 300

Val Cys Pro Val Glu Tyr Arg Ser Asp Val Asn Ser Phe Val Thr Glu
305                 310                 315                 320

Cys Glu Pro Ser Glu Leu Phe Gln Leu Gln Thr Tyr Ser Leu Pro Pro
                325                 330                 335
```

-continued

```
Phe Leu Lys Ala Val Leu Arg Gln Glu Arg Val Ser Leu Tyr Pro Phe
            340                 345                 350

Gln Ile His Ser Ile Ala Leu Ser Thr Phe Ala Ser Leu Ile Gly Pro
            355                 360                 365

Phe Gly Gly Phe Phe Ala Ser Gly Phe Lys Arg Ala Phe Lys Ile Lys
            370                 375                 380

Asp Phe Ala Asn Thr Ile Pro Gly His Gly Ile Met Asp Arg Phe
385                 390                 395                 400

Asp Cys Gln Tyr Leu Met Ala Thr Phe Val His Val Tyr Ile Thr Ser
                405                 410                 415

Phe Ile Arg Gly Pro Asn Pro Ser Lys Val Leu Gln Gln Leu Leu Val
            420                 425                 430

Leu Gln Pro Glu Gln Gln Leu Asn Ile Tyr Lys Thr Leu Lys Thr His
            435                 440                 445

Leu Ile Glu Lys Gly Ile Leu Gln Pro Thr Leu Lys Val
            450                 455                 460

<210> SEQ ID NO 3
<211> LENGTH: 38
<212> TYPE: PRT
<213> ORGANISM: Drosophila

<400> SEQUENCE: 3

Lys Arg Ala Phe Lys Ile Lys Asp Phe Gly Asp Met Ile Pro Gly His
1               5                   10                  15

Gly Gly Ile Met Asp Arg Phe Asp Cys Gln Phe Leu Met Ala Thr Phe
                20                  25                  30

Val Asn Val Tyr Ile Ser
            35

<210> SEQ ID NO 4
<211> LENGTH: 38
<212> TYPE: PRT
<213> ORGANISM: Homo sapiens

<400> SEQUENCE: 4

Lys Arg Ala Phe Lys Ile Lys Asp Phe Ala Asn Thr Ile Pro Gly His
1               5                   10                  15

Gly Gly Ile Met Asp Arg Phe Asp Cys Gln Tyr Leu Met Ala Thr Phe
                20                  25                  30

Val His Val Tyr Ile Thr
            35

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cccaccatgg ccaggaatgg tatttgc                                      27

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 6
agtgatgtga attccttcgt gacag        25

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 7
ggctctagat attaatagta atcaattac        29

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 8
cctcacgcat gcaccatggt aatagc        26

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 9
ggtgcatgcg tgaggctccg gtgc        24

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 10
gtagttttca cggtacctga aatggaag        28

<210> SEQ ID NO 11
<211> LENGTH: 2488
<212> TYPE: DNA
<213> ORGANISM: Homo sapiens
<220> FEATURE:
<221> NAME/KEY: CDS
<222> LOCATION: (25)..(1359)

<400> SEQUENCE: 11

```
cgacgtcggg ccgatttttcc cagg atg aca gag ctg agg cag agg gtg gcc        51
                          Met Thr Glu Leu Arg Gln Arg Val Ala
                            1               5 cat gag ccg gtt gcg cca ccc gag gac aag gag tca gag tca gaa gca        99
His Glu Pro Val Ala Pro Pro Glu Asp Lys Glu Ser Glu Ser Glu Ala
 10                  15                  20                  25 aag gta gat gga gag act gca tcg gac agt gag agc cag gca gaa tcc       147
Lys Val Asp Gly Glu Thr Ala Ser Asp Ser Glu Ser Gln Ala Glu Ser
                 30                  35                  40 gca ccc ctg cca gtc tct gca gat gat acc ccg gag gtc ctc aat agg       195
Ala Pro Leu Pro Val Ser Ala Asp Asp Thr Pro Glu Val Leu Asn Arg
```

|     |     |     |     |     |     |     |     |     |     |     |     |     |     |     |     |     |
|---|---|---|---|---|---|---|---|---|---|---|---|---|---|---|---|---|
|     |     |     |     | 45  |     |     |     |     | 50  |     |     |     |     | 55  |     |     |
| gcc | ctt | tcc | aac | ttg | tct | tca | aga | tgg | aag | gac | tgg | tgg | gtg | aga | ggc | 243 |
| Ala | Leu | Ser | Asn | Leu | Ser | Ser | Arg | Trp | Lys | Asp | Trp | Trp | Val | Arg | Gly |     |
|     |     |     | 60  |     |     |     |     | 65  |     |     |     |     | 70  |     |     |     |
| atc | ctg | act | ttg | gcc | atg | att | gca | ttt | ttc | ttc | atc | atc | att | tac | ctg | 291 |
| Ile | Leu | Thr | Leu | Ala | Met | Ile | Ala | Phe | Phe | Phe | Ile | Ile | Ile | Tyr | Leu |     |
|     |     | 75  |     |     |     |     | 80  |     |     |     |     | 85  |     |     |     |     |
| gga | cca | atg | gtt | ttg | atg | ata | atc | gtg | atg | tgc | gtt | cag | att | aag | tgt | 339 |
| Gly | Pro | Met | Val | Leu | Met | Ile | Ile | Val | Met | Cys | Val | Gln | Ile | Lys | Cys |     |
| 90  |     |     |     |     | 95  |     |     |     |     | 100 |     |     |     |     | 105 |     |
| ttc | cat | gag | ata | atc | act | att | ggc | tac | aac | gtc | tac | cac | tca | tat | gat | 387 |
| Phe | His | Glu | Ile | Ile | Thr | Ile | Gly | Tyr | Asn | Val | Tyr | His | Ser | Tyr | Asp |     |
|     |     |     |     | 110 |     |     |     |     | 115 |     |     |     |     | 120 |     |     |
| ctg | ccc | tgg | ttc | agg | acg | ctc | agc | tgg | tac | ttt | ctc | ctg | tgt | gta | aac | 435 |
| Leu | Pro | Trp | Phe | Arg | Thr | Leu | Ser | Trp | Tyr | Phe | Leu | Leu | Cys | Val | Asn |     |
|     |     |     | 125 |     |     |     |     | 130 |     |     |     |     | 135 |     |     |     |
| tat | ttc | ttc | tat | ggt | gag | aca | gtg | acg | gat | tac | ttc | ttc | acc | ctg | gtc | 483 |
| Tyr | Phe | Phe | Tyr | Gly | Glu | Thr | Val | Thr | Asp | Tyr | Phe | Phe | Thr | Leu | Val |     |
|     |     | 140 |     |     |     |     | 145 |     |     |     |     | 150 |     |     |     |     |
| cag | aga | gaa | gag | cct | ttg | cgg | att | ctc | agt | aaa | tac | cac | cgg | ttc | att | 531 |
| Gln | Arg | Glu | Glu | Pro | Leu | Arg | Ile | Leu | Ser | Lys | Tyr | His | Arg | Phe | Ile |     |
|     | 155 |     |     |     |     | 160 |     |     |     |     | 165 |     |     |     |     |     |
| tcc | ttt | act | ctc | tat | cta | ata | gga | ttc | tgc | atg | ttt | gta | ctg | agt | ctg | 579 |
| Ser | Phe | Thr | Leu | Tyr | Leu | Ile | Gly | Phe | Cys | Met | Phe | Val | Leu | Ser | Leu |     |
| 170 |     |     |     |     | 175 |     |     |     |     | 180 |     |     |     |     | 185 |     |
| gtc | aag | aag | cat | tat | cga | ctg | cag | ttc | tac | atg | ttt | ggc | tgg | acc | cat | 627 |
| Val | Lys | Lys | His | Tyr | Arg | Leu | Gln | Phe | Tyr | Met | Phe | Gly | Trp | Thr | His |     |
|     |     |     |     | 190 |     |     |     |     | 195 |     |     |     |     | 200 |     |     |
| gtg | aca | ttg | ctg | att | gtt | gta | aca | cag | tca | cat | ctt | gtt | atc | cac | aac | 675 |
| Val | Thr | Leu | Leu | Ile | Val | Val | Thr | Gln | Ser | His | Leu | Val | Ile | His | Asn |     |
|     |     |     | 205 |     |     |     |     | 210 |     |     |     |     | 215 |     |     |     |
| cta | ttt | gaa | gga | atg | atc | tgg | ttc | att | gtc | ccc | ata | tct | tgt | gtg | atc | 723 |
| Leu | Phe | Glu | Gly | Met | Ile | Trp | Phe | Ile | Val | Pro | Ile | Ser | Cys | Val | Ile |     |
|     |     | 220 |     |     |     |     | 225 |     |     |     |     | 230 |     |     |     |     |
| tgt | aat | gac | atc | atg | gcc | tat | atg | ttt | ggc | ttt | ttc | ttt | ggt | cgg | acc | 771 |
| Cys | Asn | Asp | Ile | Met | Ala | Tyr | Met | Phe | Gly | Phe | Phe | Phe | Gly | Arg | Thr |     |
|     | 235 |     |     |     |     | 240 |     |     |     |     | 245 |     |     |     |     |     |
| cca | ctc | atc | aag | ctg | tcc | ccg | aag | aag | acc | tgg | gaa | ggc | ttc | att | ggg | 819 |
| Pro | Leu | Ile | Lys | Leu | Ser | Pro | Lys | Lys | Thr | Trp | Glu | Gly | Phe | Ile | Gly |     |
| 250 |     |     |     |     | 255 |     |     |     |     | 260 |     |     |     |     | 265 |     |
| ggc | ttc | ttt | gct | act | gtg | gtg | ttt | ggc | ctt | ctg | ctg | tcc | tat | gtg | atg | 867 |
| Gly | Phe | Phe | Ala | Thr | Val | Val | Phe | Gly | Leu | Leu | Leu | Ser | Tyr | Val | Met |     |
|     |     |     |     | 270 |     |     |     |     | 275 |     |     |     |     | 280 |     |     |
| tcc | ggg | tac | aga | tgc | ttt | gtc | tgc | cct | gtg | gag | tac | aac | aat | gac | acc | 915 |
| Ser | Gly | Tyr | Arg | Cys | Phe | Val | Cys | Pro | Val | Glu | Tyr | Asn | Asn | Asp | Thr |     |
|     |     |     | 285 |     |     |     |     | 290 |     |     |     |     | 295 |     |     |     |
| aac | agc | ttc | act | gtg | gac | tgt | gag | ccc | tcg | gac | ctg | ttt | cgc | ctg | cag | 963 |
| Asn | Ser | Phe | Thr | Val | Asp | Cys | Glu | Pro | Ser | Asp | Leu | Phe | Arg | Leu | Gln |     |
|     |     | 300 |     |     |     |     | 305 |     |     |     |     | 310 |     |     |     |     |
| gag | tac | aac | att | cct | ggg | gtg | atc | cag | tca | gtc | att | ggc | tgg | aaa | acg | 1011 |
| Glu | Tyr | Asn | Ile | Pro | Gly | Val | Ile | Gln | Ser | Val | Ile | Gly | Trp | Lys | Thr |     |
|     | 315 |     |     |     |     | 320 |     |     |     |     | 325 |     |     |     |     |     |
| gtc | cgg | atg | tac | ccc | ttc | cag | att | cac | agc | atc | gct | ctc | tcc | acc | ttt | 1059 |
| Val | Arg | Met | Tyr | Pro | Phe | Gln | Ile | His | Ser | Ile | Ala | Leu | Ser | Thr | Phe |     |
| 330 |     |     |     |     | 335 |     |     |     |     | 340 |     |     |     |     | 345 |     |
| gcc | tcg | ctc | att | ggc | ccc | ttt | gga | gga | ttc | ttc | gca | agt | gga | ttc | aaa | 1107 |
| Ala | Ser | Leu | Ile | Gly | Pro | Phe | Gly | Gly | Phe | Phe | Ala | Ser | Gly | Phe | Lys |     |
|     |     |     |     | 350 |     |     |     |     | 355 |     |     |     |     | 360 |     |     |
| cga | gcc | ttt | aaa | atc | aaa | gac | ttt | gcc | aat | acc | att | cct | ggc | cat | gga | 1155 |

```
                Arg Ala Phe Lys Ile Lys Asp Phe Ala Asn Thr Ile Pro Gly His Gly
                                365                 370                 375 gcc atc atg gat cgc ttt gac tgc cag tat ctg atg gcc acc ttt gtc        1203
Gly Ile Met Asp Arg Phe Asp Cys Gln Tyr Leu Met Ala Thr Phe Val
            380                 385                 390 aat gta tac atc gcc agt ttt atc aga ggc cct aac cca agc aaa ctg        1251
Asn Val Tyr Ile Ala Ser Phe Ile Arg Gly Pro Asn Pro Ser Lys Leu
    395                 400                 405 att cag cag ttc ctg act tta cgg cca gat cag cag ctc cac atc ttc        1299
Ile Gln Gln Phe Leu Thr Leu Arg Pro Asp Gln Gln Leu His Ile Phe
410                 415                 420                 425 aac acg ctg cgg tct cat ctg atc gac aaa ggg atg ctg aca tcc acc        1347
Asn Thr Leu Arg Ser His Leu Ile Asp Lys Gly Met Leu Thr Ser Thr
                430                 435                 440 aca gag gac gag tagggccac ccagggccag gagaacagga acagaactga             1399
Thr Glu Asp Glu
            445 gcagggcag gtctccaagg caagcccagc tggtgtgact tagacaatga cgaggcttca       1459
actcactgtc ttttttttt ttttttttt ggagggtatt ttttatttgt gggttcaaaa        1519
aatctgtata tacagtctat gtgtttagaa tttgtgttgt aagtaaacta cagctttgag      1579
ttggaaagaa gtcacgggtt gtaaaaccat ttggattttt ttaaaacaaa agtattaata      1639
atctggaaga cagtgttgcc caggtcagga gtgttttctt ggtggttcca gcccccatca      1699
attgaactgt ttctgggctc agtcagacac agacattcat ctgtgtctga ccaaatcagg      1759
ggacttcccc acctgtggtg ggaggcacag cttagatgtt ttgtacacct ggtctttct       1819
agaaatccct gcttggagct gcagaagggt tgccttctgt aggtcggagg aatggaggct      1879
tactaaccag gtaagccttc tatgcatcca caccaaaatc ctgcagaatg taagtaagct      1939
ctgctttata agatgggttc accttcatcg cagactgaaa gtttcagttt ttatttttt      1999
cagaaagcac gaaaaattat ttataatagt ctggagaaaa aacacactgt aatatttcaa      2059
gtgtatgcag tagaatgtac tgtaactgag ccctttccca catgtctagg ctccaatgtc      2119
tcctgtaggt ccacctaact gtgtgttttc agggacaatg ccatccatgt ttgtgctgta      2179
gacttgctgc tgctgaatcc tttctgggga ctttctcatc gggcagggag cagagggctt      2239
ctcgttcatg caccctttgc ctgaacaccc atgtagctgc tgtgttgtgt atatattact      2299
cttaagagga gtgtgtgtgt ctgtgtttgt tttaaaagtc acttatttct tacagtgatt      2359
tcaattgcac catgacttct tcactaaaac cacaaagtcc tgcttaaaac tatggaaaac      2419
ctaacctgat tagagccttg actatttga agattaaatg cacacttttt atataaaaaa      2479
aaaaaaaaa                                                              2488

<210> SEQ ID NO 12
<211> LENGTH: 445
<212> TYPE: PRT
<213> ORGANISM: Homo sapiens

<400> SEQUENCE: 12

Met Thr Glu Leu Arg Gln Arg Val Ala His Glu Pro Val Ala Pro Pro
  1               5                  10                  15

Glu Asp Lys Glu Ser Glu Ser Glu Ala Lys Val Asp Gly Glu Thr Ala
             20                  25                  30

Ser Asp Ser Glu Ser Gln Ala Glu Ser Ala Pro Leu Pro Val Ser Ala
         35                  40                  45

Asp Asp Thr Pro Glu Val Leu Asn Arg Ala Leu Ser Asn Leu Ser Ser
```

```
                50                      55                      60
Arg Trp Lys Asp Trp Trp Val Arg Gly Ile Leu Thr Leu Ala Met Ile
 65                  70                      75                      80

Ala Phe Phe Phe Ile Ile Ile Tyr Leu Gly Pro Met Val Leu Met Ile
                     85                      90                      95

Ile Val Met Cys Val Gln Ile Lys Cys Phe His Glu Ile Ile Thr Ile
                    100                     105                     110

Gly Tyr Asn Val Tyr His Ser Tyr Asp Leu Pro Trp Phe Arg Thr Leu
                    115                     120                     125

Ser Trp Tyr Phe Leu Leu Cys Val Asn Tyr Phe Phe Tyr Gly Glu Thr
            130                     135                     140

Val Thr Asp Tyr Phe Phe Thr Leu Val Gln Arg Glu Glu Pro Leu Arg
145                     150                     155                     160

Ile Leu Ser Lys Tyr His Arg Phe Ile Ser Phe Thr Leu Tyr Leu Ile
                    165                     170                     175

Gly Phe Cys Met Phe Val Leu Ser Leu Val Lys Lys His Tyr Arg Leu
                    180                     185                     190

Gln Phe Tyr Met Phe Gly Trp Thr His Val Thr Leu Leu Ile Val Val
                    195                     200                     205

Thr Gln Ser His Leu Val Ile His Asn Leu Phe Glu Gly Met Ile Trp
            210                     215                     220

Phe Ile Val Pro Ile Ser Cys Val Ile Cys Asn Asp Ile Met Ala Tyr
225                     230                     235                     240

Met Phe Gly Phe Phe Phe Gly Arg Thr Pro Leu Ile Lys Leu Ser Pro
                    245                     250                     255

Lys Lys Thr Trp Glu Gly Phe Ile Gly Gly Phe Phe Ala Thr Val Val
                    260                     265                     270

Phe Gly Leu Leu Leu Ser Tyr Val Met Ser Gly Tyr Arg Cys Phe Val
                    275                     280                     285

Cys Pro Val Glu Tyr Asn Asn Asp Thr Asn Ser Phe Thr Val Asp Cys
            290                     295                     300

Glu Pro Ser Asp Leu Phe Arg Leu Gln Glu Tyr Asn Ile Pro Gly Val
305                     310                     315                     320

Ile Gln Ser Val Ile Gly Trp Lys Thr Val Arg Met Tyr Pro Phe Gln
                    325                     330                     335

Ile His Ser Ile Ala Leu Ser Thr Phe Ala Ser Leu Ile Gly Pro Phe
                    340                     345                     350

Gly Gly Phe Phe Ala Ser Gly Phe Lys Arg Ala Phe Lys Ile Lys Asp
                    355                     360                     365

Phe Ala Asn Thr Ile Pro Gly His Gly Gly Ile Met Asp Arg Phe Asp
            370                     375                     380

Cys Gln Tyr Leu Met Ala Thr Phe Val Asn Val Tyr Ile Ala Ser Phe
385                     390                     395                     400

Ile Arg Gly Pro Asn Pro Ser Lys Leu Ile Gln Gln Phe Leu Thr Leu
                    405                     410                     415

Arg Pro Asp Gln Gln Leu His Ile Phe Asn Thr Leu Arg Ser His Leu
                    420                     425                     430

Ile Asp Lys Gly Met Leu Thr Ser Thr Thr Glu Asp Glu
                    435                     440                     445

<210> SEQ ID NO 13
<211> LENGTH: 2103
<212> TYPE: DNA
<213> ORGANISM: Homo sapiens
```

-continued

<400> SEQUENCE: 13

```
tctatggtgg ggccgcgtta gtggctgcgg ctccgcggga ctccagggcg cggctgcgag      60
gtggcgggc gccccgcctg cagaaccctg cttgcagctc aggtttcggg gtgcttgagg     120
aggccgccac ggcagcgcgg gagcggaaga tgttggagct gaggcaccgg ggaagctgcc    180
ccggccccag ggaagcggtg tcgccgccac accgcgaggg agaggcggcc ggcggcgacc    240
acgaaaccga gagcaccagc gacaaagaaa cagatattga tgacagatat ggagatttgg    300
attccagaac agattctgat attccggaaa ttccaccatc ctcagataga accctgaga     360
ttctcaaaaa agctctatct ggtttatctt caaggtggaa aaactggtgg atacgtggaa    420
ttctcactct aactatgatc tcgttgtttt tcctgatcat ctatatggga tccttcatgc    480
tgatgcttct tgttctgggc atccaagtga atgcttcca tgaaattatc actataggtt     540
atagagtcta tcattcttat gatctaccat ggtttagaac actaagttgg tactttctat    600
tgtgtgtaaa ctactttttc tatggagaga ctgtagctga ttattttgct acatttgttc    660
aaagagaaga acaacttcag ttcctcattc gctaccatag atttatatca tttgccctct    720
atctggcagg tttctgcatg tttgtactga gtttggtgaa ggaacattat cgtctgcagt    780
tttatatgtt cgcatggact catgtcactt tactgataac tgtcactcag tcacaccttg    840
tcatccaaaa tctgtttgaa ggcatgatat ggttccttgt tccaatatca agtgttatct    900
gcaatgacat aactgcttac ctttttggat ttttttttgg gagaactcca ttaattaagt    960
tgtctcctaa aaagacttgg gaaggattca ttggtggttt cttttccaca gttgtgtttg   1020
gattcattgc tgcctatgtg ttatccaaat accagtactt tgtctgccca gtggaatacc   1080
gaagtgatgt aaactccttc gtgacagaat gtgagccctc agaacttttc cagcttcaga   1140
cttactcact tccacccttt ctaaaggcag tcttgagaca ggaaagagtg agcttgtacc   1200
cttttccagat ccacagcatt gcactgtcaa cctttgcatc tttaattggc ccatttggag   1260
gcttctttgc tagtggattc aaaagagcct tcaaaatcaa ggattttgca ataccattc    1320
ctggacatgg tgggataatg gacagatttg attgtcagta tttgatggca acttttgtac   1380
atgtgtacat cacaagtttt ataagggggcc caaatcccag caaagtgcta cagcagttgt   1440
tggtgcttca acctgaacag cagttaaaata tatataaac cctgaagact catctcattg    1500
agaaaggaat cctacaaccc accttgaagg tataactgga tccagagagg aaggactga    1560
caagaaggaa ttattcagaa aaacactgac agatgtttta taaattgtac agaaaaatag    1620
ttaaaaatgc aataggttga agttttggag atatgtttct ctctgaaatt actgtgaata    1680
tttaacaaac acttacttga tctatgttat gaaataagta gcaaattgcc agcaaaatgt    1740
cttgtacctt ttctaaagtg tattttctga tgtgaacttc cttcccctta cttgctaggt   1800
ttcataattt aaaagactgg tatttaaaag agtcaaacac tataaaatga gtaagttgac   1860
gatgttttaa gattgcacct ggcagtgtgc cttttttgcac aaatatttac ttttgcactt   1920
ggagctgctt ttaattttag caaatgtttt tatgcaaggc acaataggaa gtcagttctc    1980
ctgcacttcc tcctcatgta gtctggagta cttttctaaag ggcttagttg gatttaaaaa   2040
aaaaaaaaaa agggcggccg ctctagagga tcctcgagg ggcccaagct tacgcgtgca   2100
tgc                                                                 2103
```

<210> SEQ ID NO 14
<211> LENGTH: 45
<212> TYPE: PRT

<213> ORGANISM: Homo sapiens

<400> SEQUENCE: 14

```
Gln Ser His Leu Val Ile His Asn Leu Phe Glu Gly Met Ile Trp Phe
 1               5                  10                  15

Ile Val Pro Ile Ser Cys Val Ile Cys Asn Asp Ile Met Ala Tyr Met
                20                  25                  30

Phe Gly Phe Phe Phe Gly Arg Thr Pro Leu Ile Lys Leu
            35                  40                  45
```

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 15
aggacgcata tgagtggtag ac                                               22

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 16
gactctagcc taggcttttg c                                                21

<210> SEQ ID NO 17
<211> LENGTH: 249
<212> TYPE: PRT
<213> ORGANISM: E. coli

<400> SEQUENCE: 17

```
Met Leu Ala Ala Trp Glu Trp Gly Gln Leu Ser Gly Phe Thr Thr Arg
 1               5                  10                  15

Ser Gln Arg Val Trp Leu Ala Val Leu Cys Gly Leu Leu Leu Ala Leu
                20                  25                  30

Met Leu Phe Leu Leu Pro Glu Tyr His Arg Asn Ile His Gln Pro Leu
            35                  40                  45

Val Glu Ile Ser Leu Trp Ala Ser Leu Gly Trp Trp Ile Val Ala Leu
        50                  55                  60

Leu Leu Val Leu Phe Tyr Pro Gly Ser Ala Ala Ile Trp Arg Asn Ser
 65                 70                  75                  80

Lys Thr Leu Arg Leu Ile Phe Gly Val Leu Thr Ile Val Pro Phe Phe
                85                  90                  95

Trp Gly Met Leu Ala Leu Arg Ala Trp His Tyr Asp Glu Asn His Tyr
            100                 105                 110

Ser Gly Ala Ile Trp Leu Leu Tyr Val Met Ile Leu Val Trp Gly Ala
        115                 120                 125

Asp Ser Gly Ala Tyr Met Phe Gly Lys Leu Phe Gly Lys His Lys Leu
    130                 135                 140

Ala Pro Lys Val Ser Pro Gly Lys Thr Trp Gln Gly Phe Ile Gly Gly
145                 150                 155                 160

Leu Ala Thr Ala Ala Val Ile Ser Trp Gly Tyr Gly Met Trp Ala Asn
                165                 170                 175
```

Leu Asp Val Ala Pro Val Thr Leu Leu Ile Cys Ser Ile Val Ala Ala
        180                 185                 190

Leu Ala Ser Val Leu Gly Asp Leu Thr Glu Ser Met Phe Lys Arg Glu
        195                 200                 205

Ala Gly Ile Lys Asp Ser Gly His Leu Ile Pro Gly His Gly Gly Ile
        210                 215                 220

Leu Asp Arg Ile Asp Ser Leu Thr Ala Ala Val Pro Val Phe Ala Cys
225                 230                 235                 240

Leu Leu Leu Leu Val Phe Arg Thr Leu
                245

<210> SEQ ID NO 18
<211> LENGTH: 457
<212> TYPE: PRT
<213> ORGANISM: Yeast

<400> SEQUENCE: 18

Met Ser Asp Asn Pro Glu Met Lys Pro His Gly Thr Ser Lys Glu Ile
  1               5                  10                  15

Val Glu Ser Val Thr Asp Ala Thr Ser Lys Ala Ile Asp Lys Leu Gln
                 20                  25                  30

Glu Glu Leu His Lys Asp Ala Ser Glu Ser Val Thr Pro Val Thr Lys
             35                  40                  45

Glu Ser Thr Ala Ala Thr Lys Glu Ser Arg Lys Tyr Asn Phe Phe Ile
 50                  55                  60

Arg Thr Val Trp Thr Phe Val Met Ile Ser Gly Phe Phe Ile Thr Leu
 65                  70                  75                  80

Ala Ser Gly His Ala Trp Cys Ile Val Leu Ile Leu Gly Cys Gln Ile
                 85                  90                  95

Ala Thr Phe Lys Glu Cys Ile Ala Val Thr Ser Ala Ser Gly Arg Glu
                100                 105                 110

Lys Asn Leu Pro Leu Thr Lys Thr Leu Asn Trp Tyr Leu Leu Phe Thr
            115                 120                 125

Thr Ile Tyr Tyr Leu Asp Gly Lys Ser Leu Phe Lys Phe Phe Gln Ala
        130                 135                 140

Thr Phe Tyr Glu Tyr Pro Val Leu Asn Phe Ile Val Thr Asn His Lys
145                 150                 155                 160

Phe Ile Cys Tyr Cys Leu Tyr Leu Met Gly Phe Val Leu Phe Val Cys
                165                 170                 175

Ser Leu Arg Lys Gly Phe Leu Lys Phe Gln Phe Gly Ser Leu Cys Val
            180                 185                 190

Thr His Met Val Leu Leu Val Val Phe Gln Ala His Leu Ile Ile
        195                 200                 205

Lys Asn Val Leu Asn Gly Leu Phe Trp Phe Leu Leu Pro Cys Gly Leu
        210                 215                 220

Val Ile Val Asn Asp Ile Phe Ala Tyr Leu Cys Gly Ile Thr Phe Gly
225                 230                 235                 240

Lys Thr Lys Leu Ile Glu Ile Ser Pro Lys Lys Thr Leu Glu Gly Phe
                245                 250                 255

Leu Gly Ala Trp Phe Phe Thr Ala Leu Ala Ser Ile Ile Leu Thr Arg
            260                 265                 270

Ile Leu Ser Pro Tyr Thr Tyr Leu Thr Cys Pro Val Glu Asp Leu His
        275                 280                 285

Thr Asn Phe Phe Ser Asn Leu Thr Cys Glu Leu Asn Pro Val Phe Leu
290                 295                 300

-continued

Pro Gln Val Tyr Arg Leu Pro Pro Ile Phe Phe Asp Lys Val Gln Ile
305                 310                 315                 320

Asn Ser Ile Thr Val Lys Pro Ile Tyr Phe His Ala Leu Asn Leu Ala
            325                 330                 335

Thr Phe Ala Ser Leu Phe Ala Pro Phe Gly Gly Phe Phe Ala Ser Gly
            340                 345                 350

Leu Lys Arg Thr Phe Lys Val Lys Asp Phe Gly His Ser Ile Pro Gly
            355                 360                 365

His Gly Gly Ile Thr Asp Arg Val Asp Cys Gln Phe Ile Met Gly Ser
    370                 375                 380

Phe Ala Asn Leu Tyr Tyr Glu Thr Phe Ile Ser Glu His Arg Ile Thr
385                 390                 395                 400

Val Asp Thr Val Leu Ser Thr Ile Leu Met Asn Leu Asn Asp Lys Gln
            405                 410                 415

Ile Ile Glu Leu Ile Asp Ile Leu Ile Arg Phe Leu Ser Lys Lys Gly
            420                 425                 430

Ile Ile Ser Ala Lys Asn Phe Glu Lys Leu Ala Asp Ile Phe Asn Val
            435                 440                 445

Thr Lys Lys Ser Leu Thr Asn His Ser
    450                 455

<210> SEQ ID NO 19
<211> LENGTH: 446
<212> TYPE: PRT
<213> ORGANISM: Drosophila

<400> SEQUENCE: 19

Met Ala Glu Val Arg Arg Lys Gly Glu Asp Glu Pro Leu Glu Asp
1               5                   10                  15

Thr Ala Ile Ser Gly Ser Asp Ala Ala Asn Lys Arg Asn Ser Ala Ala
            20                  25                  30

Asp Ser Ser Asp His Val Asp Ser Glu Glu Lys Ile Pro Glu Glu
            35                  40                  45

Lys Phe Val Asp Glu Leu Ala Lys Asn Leu Pro Gln Gly Thr Asp Lys
    50                  55                  60

Thr Pro Glu Ile Leu Asp Ser Ala Leu Lys Asp Leu Pro Asp Arg Trp
65                  70                  75                  80

Lys Asn Trp Val Ile Arg Gly Ile Phe Thr Trp Ile Met Ile Cys Gly
                85                  90                  95

Phe Ala Leu Ile Ile Tyr Gly Gly Pro Leu Ala Leu Met Ile Thr Thr
            100                 105                 110

Leu Leu Val Gln Val Lys Cys Phe Gln Glu Ile Ile Ser Ile Gly Tyr
        115                 120                 125

Gln Val Tyr Arg Ile His Gly Leu Pro Trp Phe Arg Ser Leu Ser Trp
    130                 135                 140

Tyr Phe Leu Leu Thr Ser Asn Tyr Phe Tyr Gly Glu Asn Leu Val
145                 150                 155                 160

Asp Tyr Phe Gly Val Val Ile Asn Arg Val Glu Tyr Leu Lys Phe Leu
                165                 170                 175

Val Thr Tyr His Arg Phe Leu Ser Phe Ala Leu Tyr Ile Ile Gly Phe
            180                 185                 190

Val Trp Phe Val Leu Ser Leu Val Lys Lys Tyr Tyr Ile Lys Gln Phe
        195                 200                 205

Ser Leu Phe Ala Trp Thr His Val Ser Leu Leu Ile Val Val Thr Gln

-continued

```
            210                 215                 220
Ser Tyr Leu Ile Ile Gln Asn Ile Phe Glu Gly Leu Ile Trp Phe Ile
225                 230                 235                 240

Val Pro Val Ser Met Ile Val Cys Asn Asp Val Met Ala Tyr Val Phe
                245                 250                 255

Gly Phe Phe Phe Gly Arg Thr Pro Leu Ile Lys Leu Ser Pro Lys Lys
                260                 265                 270

Thr Trp Glu Gly Phe Ile Gly Gly Phe Ala Thr Val Leu Phe Gly
            275                 280                 285

Ile Leu Phe Ser Tyr Val Leu Cys Asn Tyr Gln Tyr Phe Ile Cys Pro
            290                 295                 300

Ile Gln Tyr Ser Glu Glu Gln Gly Arg Met Thr Met Ser Cys Val Pro
305                 310                 315                 320

Ser Tyr Leu Phe Thr Pro Gln Glu Tyr Ser Leu Lys Leu Phe Gly Ile
                325                 330                 335

Gly Lys Thr Leu Asn Leu Tyr Pro Phe Ile Trp His Ser Ile Ser Leu
                340                 345                 350

Ser Leu Phe Ser Ser Ile Ile Gly Pro Phe Gly Gly Phe Phe Ala Ser
            355                 360                 365

Gly Phe Lys Arg Ala Phe Lys Ile Lys Asp Phe Gly Asp Met Ile Pro
            370                 375                 380

Gly His Gly Gly Ile Met Asp Arg Phe Asp Cys Gln Phe Leu Met Ala
385                 390                 395                 400

Thr Phe Val Asn Val Tyr Ile Ser Phe Ile Arg Thr Pro Ser Pro Ala
                405                 410                 415

Lys Leu Leu Thr Gln Ile Tyr Asn Leu Lys Pro Asp Gln Gln Tyr Gln
                420                 425                 430

Ile Tyr Gln Ser Leu Lys Asp Asn Leu Gly His Met Leu Thr
            435                 440                 445
```

MAMMALIAN CDP-DIACYLGLYCEROL SYNTHASE

TECHNICAL FIELD OF THE INVENTION

This present invention provides cDNA sequences and polypeptides having the enzyme CDP-diacylglycerol synthase (CDS) activity. CDS is also known as CTP:phosphatidate cytidyltransferase (EC2.7.7.41). The present invention further provides for isolation and production of polypeptides involved in phosphatidic acid metabolism and signaling in mammalian cells, in particular, the production of purified forms of CDS.

BACKGROUND OF THE INVENTION

CDP-diacylglycerol (DAG) is an important branch point intermediate just downstream of phosphatidic acid (PA) in the pathways for biosynthesis of glycerophosphate-based phospholipids (Kent, Anal. Rev. Biocheni. 64: 315–343, 1995). In eukaryotic cells, PA, the precursor molecule for all glycerophospholipid, is converted either to CDP-DAG by CDP-DAG synthase (CDS) or to DAG by a phosphohydrolase. In mammalian cells, CDP-DAG is the precursor to phosphatidylinositol (PI), phosphatidylglycerol (PG), and cardiolipin (CL). Diacylglycerol is the precursor to triacylglycerol, phosphatidylethanolamine, and phosphatidylcholine in eukaryotic cells. Therefore, the partitioning of phosphatidic acid between CDP-diacylglycerol and diacylglycerol must be an important regulatory point in eukaryotic phospholipid metabolism (Shen et al., J. Biol. Chem. 271:789–795, 1996). In eukaryotic cells, CDP-diacylglycerol is required in the mitochondria for phosphatidylglycerol and cardiolipin synthesis and in the endoplasmic reticulum and possibly other organelles for the synthesis of phosphatidylinositol (PI). PI, in turn, is the precursor for the synthesis of a series of lipid second messengers, such as phosphatidylinositol-4,5-bisphosphate ($PIP_2$), DAG and inositol-1,4,5-trisphosphate ($IP_3$). Specifically, PIP2 is the substrate for phospholipase C that is activated in response to a wide variety of extracellular stimuli, leading to the generation of two lipid second messengers; namely, DAG for the activation of protein kinase C and 1P3 for the release of $Ca^{++}$ from internal stores (Dowhan, Anal. Rev. Biochem. 66: 199–232, 1997).

The genes coding for CDS have been identified in E. coli (Icho et al, J. Biol. Chem. 260: 12078–12083, 1985), in yeast (Shen et al., J. Biol. Chem. 271:789–795, 1996), and in Drosophila (Wu et al., Nature 373:216–222, 1995). A human cDNA coding for CDS (hCDS1) is described by us herein and has been reported in Weeks et al., DNA Cell Biol. 16: 281–289, 1997. Moreover, Heacock et al., J. Neurochem. 67: 2200–2203, 1997 report cloning of a CDS1 from a human neuronal cell line. Furthermore, Lykidis et al., J. Biol. Chem 272:33402–33409 ,1997 and Halford et al., Genomics 54:140–144, 1998 both report DNA sequences suspected to encode a human cds2 protein, but these references fail to disclose either biological activity or an intact N-terminal region for the putative proteins.

It is of interest to isolate polynucleotides coding for human CDS and express them in mammalian cells to determine the potential roles of this enzyme in cellular function and use this enzyme as a target for the development of specific compounds that are modulators of its activity. With the advance in the understanding of disease processes, it has been found that many diseases result from the malfunction of intracellular signaling. This recognition has led to research and development of therapies based on the interception of signaling pathways in diseases (Levitzki, Curr. Opin. Cell Biol. 8:239–244, 1996). Compounds that modulate CDS activity, and hence modulate generation of a variety of lipid second messengers and signals involved in cell activation, are therefore of therapeutic interest generally, and of particular interest in the areas of inflammation and oncology:

SUMMARY OF THE INVENTION

The present invention provides cDNA sequences, polypeptide sequences, and transformed cells for producing isolated recombinant mammalian CDS. The present invention provides two novel human polypeptides and fragment thereof, having CDS activity. The polypeptides discovered herein are novel and will be called hCDS1 (human CDS1) and hCDS2 (human CDS2). CDS catalyzes the conversion of phosphatidic acid (PA) to CDP-diacylglycerol (CDP-DAG), which in turn is the precursor to phosphatidylinositol (PI), phosphatidylglycerol (PG) and cardiolipin (CL).

The present invention further provides nucleic acid sequences coding for expression of the novel CDS polypeptides and active fragments thereof. The invention further provides purified CDS mRNAs and antisense oligonucleotides for modulation of expression of the genes coding for CDS polypeptides. Assays for screening test compounds for their ability to modulate CDS activity are also provided.

Recombinant CDS is useful for screening candidate drug compounds that modulate CDS activity, particularly those compounds that activate or inhibit CDS activity. The present invention provides cDNA sequences encoding a polypeptide having CDS activity and comprising the DNA sequence set forth in SEQ ID NO. 1 (hCDS1), the DNA sequence (SEQ ID NO:11) set forth in FIG. 8 (hCDS2), shortened fragments thereof, or additional cDNA sequences which due to the degeneracy of the genetic code encode a polypeptide of SEQ ID NO. 2 (hCDS1), a polypeptide of FIG. 8 (hCDS2), or biologically active fragments thereof, or a sequence hybridizing thereto under high stringency conditions. The present invention further provides a polypeptide having CDS activity and comprising the amino acid sequence of SEQ ID NO. 2 (hCDS1), the amino acid sequence (SEQ ID NO:12) of FIG. 8 (hCDS2), or biologically active fragments thereof Also provided by the present invention are vectors containing a DNA sequence encoding a mammalian CDS enzyme in operative association with an expression control sequence. Host cells, transformed with such vectors for use in producing recombinant CDS are also provided with the present invention. The inventive vectors and transformed cells are employed in a process for producing recombinant mammalian CDS. In this process, a cell line transformed with a cDNA sequence encoding a CDS enzyme in operative association with an expression control sequence, is cultured. The claimed process may employ a number of known cells as host cells for expression of the CDS polypeptide, including, for example, mammalian cells, yeast cells, insect cells and bacterial cells.

Another aspect of this invention provides a method for identifying a pharmaceutically-active compound by determining if a selected compound modulates the activity of CDS for converting PA to CDP-DAG. A compound having such activity is capable of modulating signaling kinase pathways and being a pharmaceutical compound useful for augmenting trilineage hematopoiesis after cytoreductive therapy and for anti-inflammatory activity in inhibiting the inflammatory cascade following hypoxia and reoxygenation injury (e.g., sepsis, trauma, ARDS, etc.).

The present invention further provides a transformed cell that expresses active mammalian CDS and further comprises a means for determining if a drug candidate compound is therapeutically active by modulating recombinant CDS activity.

BRIEF DESCRIPTION OF THE DRAWINGS

FIGS. 1A–1F show the cDNA sequence (SEQ ID NO:13) encoding hCDS1. The nucleotide sequence analysis and restriction mapping of the cDNA clone revealed a 5'-untranslated region of 149 base pairs, an open reading frame capable of encoding a 461 amino acid polypeptide that spans nucleotide positions 150 to 1535 and a 3'-untranslated region of 520 base pairs.

FIGS. 2A–2E show the translated amino acid sequence (SEQ ID NO:1) of hCDS1.

FIGS. 3A–3C show the amino acid sequence (SEQ ID NO:12) of hCDS1.

FIG. 4 shows the sequence homology among the hCDS1 coding sequence (SEQ ID NO:2), the yeast CDS coding sequence (SEQ ID NO:18), E. coli CDS coding sequence (SEQ ID NO:17); the Drosophila CDS coding sequence (SEQ ID NO:19). This comparison shows that hCDS1 has the greatest extended homology with amino acids 109 to 448 of Drosophila CDS. The hCDS1 protein and the CDS protein from Drosophila, yeast, and E. coli have 45%, 221% and 7% overall match in amino acid sequence, respectively.

FIG. 6 is a representative phosphorimage of [$^{32}$P] phospholipids from membrane fraction CDS assay reactions after the second dimension of ffTLC. FIG. 6 confirms that the radiolabeled product found in the membrane fractions does migrate with a CDP-DAG standard on TLC. The identities of labeled bands were determined by migration of phospholipid standards visualized by UV or FL imaging on the STORM after primulin staining. Lanes 1–3 represent triplicate samples derived from membranes of NCI-H460 cells transfected with the hCDS1 expression vector, and lanes 4–6 represent triplicate samples from transfectants with the control vector. Cells transfected with the hCDS1 cDNA showed 1.6–2.4 fold more CDS activity in membrane fractions than vector transfectants. The relative CDS activity between hCDS1 transfectants and vector transfectants was similar when determined by scintillation counting or TLC analysis. These data indicate that the hCDS1 cDNA clone of SEQ ID NO. 1 does encode CDS activity.

FIGS. 7A and 7B show, respectively, that production of TNF-α (tumor necrosis factor alpha) and IL-6 in ECV304 cells stably transfected with a hCDS1 expression vector increases by greater than five fold relative to ECV304 cells stably transfected with control vector after equal stimulation with IL-1β (interleukin-1 beta). There was little effect on basal level of cytokine release. These data indicate that overexpression of hCDS1 amplified the cytokine signaling response in these cells, as opposed to enhancing steady state, basal signals.

FIGS. 8A and 8B show the DNA and amino acid sequence (SEQ ID NOS: 11 and 12) of hCDS2.

FIG. 9 shows an amino acid sequence alignment of the hCDS2 coding sequence (SEQ ID NO:12) with the hCDS1 coding sequence (SEQ ID NO:2). The amino acids that are identical between the two sequences are highlighted.

FIG. 10 shows the results of a TLS analysis of hCDS2 production of [32P]CDP-DAG after TLC analysis

DETAILED DESCRIPTION OF THE INVENTION

Figure 5:
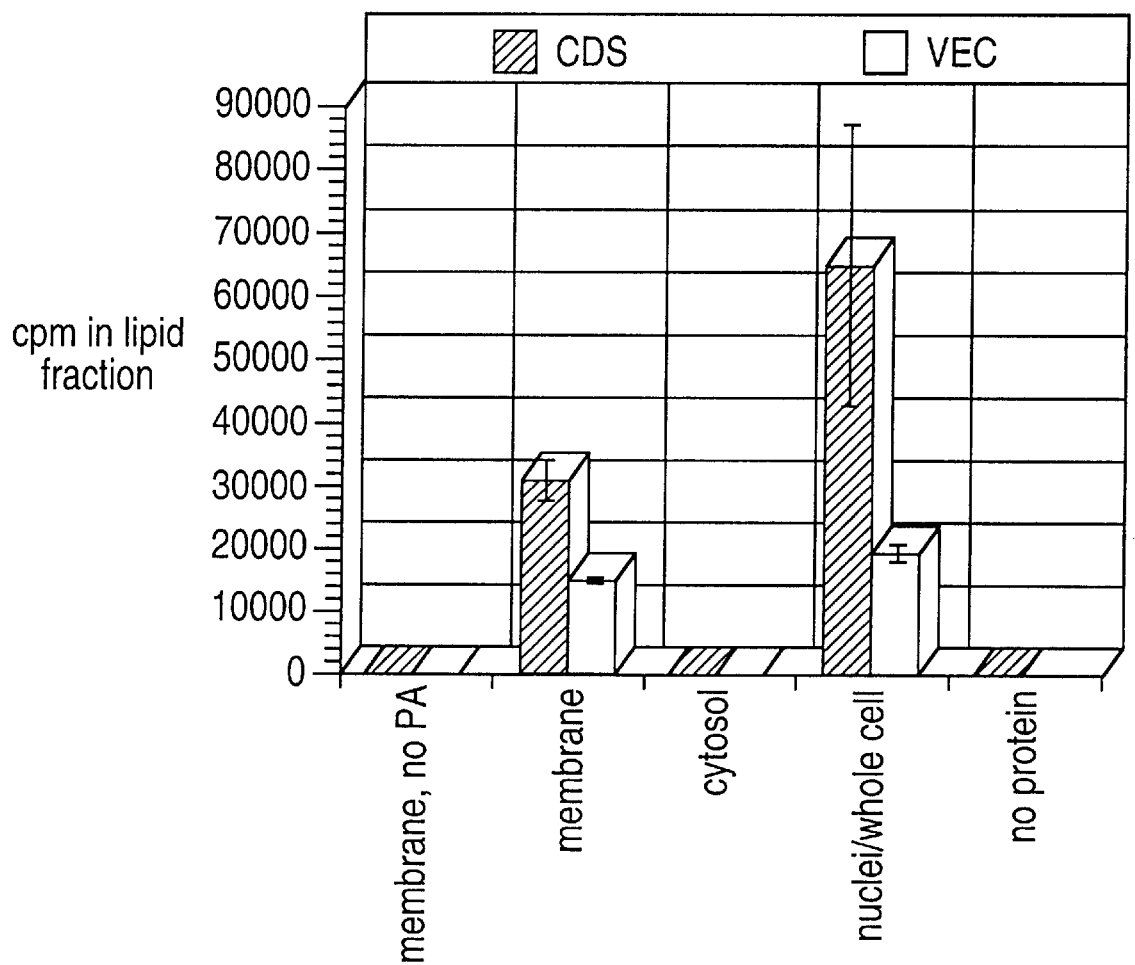
FIG. 5 shows the results of in vitro hCDS1 activity assays on cell fractions from stable transfectants of NCI-H460 cells. CDS activity was assessed by conversion of ($\alpha^{32}$P) CTP to ($^{32}$P)CDP-DAG in in vitro reactions that required addition of an exogenous PA substrate. This is a representative histogram comparing the radiolabel incorporated into various cell fractions (membranes, cytosol, and nuclei/unbroken cells) from NCI-H460 cells stably transfected with the hCDS1 cDNA (pCE2.hCDS) or vector only (pCE2). In all fractions, the hCDS1 cDNA increased radiolabel in the organic phase of the reactions. Total CDS activity was much greater in membrane fractions, as would be expected for membrane associated CDS, compared to cytosol fractions. Activity in unbroken cells masked the activity specific to nuclei.

The present invention provides novel, isolated, biologically active mammalian CDS enzymes. The term "isolated" means any CDS polypeptide of the present invention, or any other gene encoding CDS polypeptide, which is essentially free of other polypeptides or genes, respectively, or of other contaminants with which the CDS polypeptide or gene might normally be found in nature.

The invention includes a biologically active polypeptide, CDS, and biologically active fragments thereof As used herein, the term "biologically active polypeptide" refers to a polypeptide which possesses a biological function or activity which is identified through a biological assay, preferably cell-based, and which results in the formation of CDS-DAG species from PA. A "biologically active polynucleotide" denotes a polynucleotide which encodes a biologically active polypeptide. The term "biologically active fragment," as used herein, refers to a nucleotide or polypeptide sequence in which one or more amino acids or nucleotides has been deleted but which retains CDS activity.

Minor modification of the CDS primary amino acid sequence may result in proteins which have substantially equivalent activity as compared to the sequenced CDS polypeptide described herein. Such modifications may be deliberate, as by site-directed mutagenesis, or may be spontaneous. All of the polypeptides produced by these modifications are included herein as long as the activity of CDS is present. This can lead to the development of a smaller active molecule which would have broader utility. For example, the present invention includes removal of one or more amino, carboxy terminal, or internal amino acids from the CDS polypeptide, so long as such amino acids are not required for CDS activity.

The CDS polypeptide of the present invention also includes conservative variations of the polypeptide sequence. The term "conservative variation" denotes the replacement of an amino acid residue by another, biologically active similar residue. Examples of conservative variations include the substitution of one hydrophobic residue, such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of parent amino acid provided that antibodies raised to the substituted polypeptide also immunologically react with the unsubstituted polypeptide.

The present invention further includes allelic variations (naturally-occurring base changes in the species population which may or may not result in an amino acid change) of the DNA sequences herein encoding active CDS polypeptides and active fragments thereof The inventive DNA sequences further comprise those sequences which hybridize under high stringency conditions (see, for example, Maniatis et al, *Molecular Cloning (A Laboratory Manual)*, Cold Spring Harbor Laboratory, pages 387–389, 1982) to the coding region of hCDS1 (e.g. nucldeotide #150 to nucleotide #1535 in SEQ ID NO. 1) or the coding region of hCDS2 (SEQ ID NOS 11 and 12) (FIGS. 8A and 8B) and which have CDS activity. High stringency conditions include 5×SSC at 65° C., followed by washing in 0.1×SSC at 65° C. for thirty minutes or, alternatively, 50% formamide, 5×SSC at 42° C.

The present invention also includes nucleotide sequences having at least an 85%, at least a 90%, or at least a 95% sequence identity to the nucleotide sequence of the coding region of hCDS2 (FIGS. 8A and 8B) and which have CDS activity. The present invention further includes a polypeptide having at least an 85%, at least a 90%, or at least a 95% sequence identity to the hCDS2 polypeptide shown in FIG. 8 and which have CDS activity. As used herein, the term "sequence identity" denotes the "match percentage" calculated by the DNASIS computer program (Version 2.5 for Windows; available from Hitachi Software Engineering Co., Ltd., South San Francisco, Calif.) using standard defaults as described in the reference manual accompanying the software, which is incorporated herein by reference.

With regard to the above-described fragments of hCDS2, sequences that hybridize to hCDS2, and sequences having sequence identity to hCDS2, the invention includes embodiments where these sequences have an intact CDS N-terminal region.

The present invention further includes DNA sequences which code for CDS polypeptides having CDS activity but differ in codon sequence due to degeneracy of the genetic code. Variations in the DNA sequences which are caused by point mutations or by induced modifications of the sequence of SEQ ID NO. 1 or FIGS. 8A and 8B, which enhance the activity of the encoded polypeptide or production of the encoded CDS polypeptide are also encompassed by the present invention.

CDS Sequence Discovery hCDS1

A homology search of the Genbank database (Boguski, et al., *Science* 265:1993–1994, 1994) of expressed sequence tags (dbEST) using Drosophila CDS protein sequence as a probe came up with several short stretches of cDNA sequence with homology to the Drosophila CDS protein sequence. These cDNA sequences were derived from single-run partial sequencing of random human CDNA clones carried out mainly by I.M.A.G.E. Consortium [LLNL] cDNA clones program. An example of the amino acid sequence homology between the Drosophila CDS and a human cDNA clone (IMAGE Clone ID #135630) is shown below:

371 KRAFKIKDFGDMIPGHGGIMDRFDCQFL-
MATFVNVYIS 408 KRAFKIKDF+
IPGHGGIMDRFDCQ+LMATFV+VYI+11
KRAFKIKDFANTIPGHGGIMDRFDCQYL-
MATFVHVYIT 124

The top line (SEQ ID NO. 3) refers to the Drosophila CDS sequence from amino acids 371 to 408 and the bottom line (SEQ ID NO. 4) refers to a homologous region from IMAGE Clone ID #135630 translated using reading frame +2. Identical amino acids between these two sequences are shown on the middle line with the "+" signs indicating conservative amino acid changes. In order to determine if such cDNA clones with this level of homology to the Drosophila CDS sequence encoded human CDS sequence, it was necessary to isolate the full-length cDNA clone, insert it into an expression vector, and test if cells transfected with the cDNA expression vector will produce more CDS activity.

Accordingly, a synthetic oligonucleotide (o.h.cds. IR), 5'-CCCACCATGG CCAGGAATGG TATTTGC -3' (SEQ ID NO. 5), was made based on the complement sequence of the amino acid region, ANTIPGHGG (residues 10–18 of SEQ ID NO:4); of IMAGE Clone ID #135630 for the isolation of a putative human cDNA clone from a SuperScript human leukocyte cDNA library (Life Technologies, Gaithersburg, Md.) using the GeneTrapper cDNA positive selection system (Life Technologies, Gaithersburg, Md.). The colonies obtained from positive selection were screened with a $[\gamma\text{-}^{32}P]$-ATP labeled synthetic oligonucleotide (o.h.cds. 1), 5'- AGTGATGTGA ATTCCTTCGT GACAG -3' (SEQ ID NO. 6), corresponding to nucleotides 144–168 of IMAGE Clone ID #133825. Of the few cDNA clones that hybridized with the o.h.cds. 1 probe, clone LK64 contained the largest cDNA insert with a size of 1700 base pairs. DNA sequence analysis of LK64 showed the translated sequence of its largest open reading frame from the 5' end contained extensive homology with amino acids 109 to 448 of the Drosophila CDS protein sequence. Clone LK64 did not appear to contain a full-length cDNA insert for CDS. It was missing the coding region corresponding to the first 110 amino acids from the N-terminus. A second homology search of the Genbank database (Boguski, et al., *Science* 265:1993–1994, 1994) using the 3'-untranslated sequence of LK64 as a probe came up with more short stretches of cDNA sequences with perfect homology to the 3' end of the putative human CDS clone LK64. Restriction mapping and DNA sequence analysis of IMAGE Clone ID #145253 (Genome Systems, St. Louis, Mo.), derived from a placental cDNA library, showed it contained extensive sequence homology with the N-terminal coding region of the Drosophila CDS and overlapped with the sequence obtained from clone LK64.

To assemble the putative full-length human CDS cDNA clone, a 500 base pair Pst I - Nco I fragment from of IMAGE Clone ID #145253 and a 1500 base pair Nco I- Not I fragment from LK64 were isolated. These two fragments were inserted into a Pst I and Not I digested vector pBluescriptII SK(-) vector via a three-part ligation to generate pSK.hcds.

FIGS. 1A–1F show the cDNA sequence of hCDS1. The nucleotide sequence analysis and restriction mapping of the cDNA clone revealed a 5'-untranslated region of 149 base pairs, an open reading frame encoding a 461 amino acids polypeptide that spans nucleotide positions 150 to 1535 and a 3'-untranslated region of 520 base pairs (FIGS. 2A–2E). The ATG initiation site for translation was identified at nucleotide positions 150–152 and fulfilled the requirement for an adequate initiation site. (Kozak, *Critical Rev. Biochem. Mol. Biol.* 27:385–402, 1992). There was another upstream ATG at positions 4–6 but it was followed by an in-phase stop codon at positions 19–20. The calculated molecular weight of hCDS1 is 53,226 daltons with a predicted pI of 7.57.

The sequence of the 461 amino acid open reading frame (FIGS. 3A–3C) was used as the query sequence to search for homologous sequences in protein databases. A search of Genbank Release 92 from the National Center for Biotechnology Information (NCBI) using the BLAST program showed that this protein was most homologous to the Drosophila CDS, the yeast CDS, and the E. coli CDS. FIG. 4 shows amino acid sequence alignment of this putative human CDS coding sequence with the Drosophila CDS, the yeast CDS, and the E. coli coding sequences, showing that the human CDS is most homologous to the Drosophila CDS.

hCDS2

A homology search of the Genbank database (Boguski, et al., Science 265:1993–1994, 1994) of expressed sequence tags (dbEST) using the hCDS1 protein sequence (Weeks et al, DNA Cell Biol. 16: 281–289, 1997) as probe came up with several short stretches of human cDNA sequences that were homologous but distinct from the hCDS1 sequence. These cDNA sequences were derived from single-run partial sequencing of random human cDNA clones projects carried out mainly by I.M.A.G.E. Consortium [LLNL] cDNA clones program.

Of these sequences, IMAGE Clone ID#485825 was found to have the following homology to the coding region of hCDS1 from amino acids 227–271:

```
           10         20        30        40
    QSHLVIHNLFEGMIWFIVPISCVICNDIMAYMFGFFFGRTPLIKL
    X::::::.::::::::::.::::.::::::: ::..::::::::::::::
    QSHLVIQNLFEGMIWFLVPISSVICNDITAYLFGFFFGRTPLIKL
           230        240       250       260       270
```

The top line (SEQ ID NO:14) refers to IMAGE Clone ID#485825 translated using reading frame +3 and the bottom line refers to the coding region of hCDS1 (SEQ ID NO:2) from amino acids 227–271. Identical amino acids between these two sequences are shown on the middle line as ":" and with the "." signs indicating conservative amino acid changes. Since the 5'-end of the cDNA insert of IMAGE Clone ID#485825 corresponded to amino acid 227 of hCDS1, this clone therefore does not appear to contain a full-length cDNA insert for CDS, most likely missing the coding region corresponding to the first 220 amino acids from the N-terminus. A second homology search of the Genbank database (Boguski, et al., Science 265:1993–1994, 1994) of expressed sequence tags (dbEST) using the sequence of IMAGE Clone ID#485825 as probe came up with a clone with a longer cDNA insert (clone ID#663789) from the Genbank database with perfect homology to the IMAGE Clone ID#485825. Restriction mapping and DNA sequence analysis of IMAGE Clone ID#663789 (Genome Systems, St. Louis, Mo.) showed it to be a longer cDNA clone with extensive sequence homology with the coding region of hCDS1 but still missing the first 60 amino acids in the coding region. To isolate the 5'-coding region of hCDS2 cDNA, a synthetic oligonucleotide, 5'-AGGACGCATA TGAGTGGTAG AC-3' (SEQ ID NO:15) (oCDS2_2R), complementary to a region spanning the Nde I site near the 5' portion of clone ID#663789 was used in combination with a forward vector primer (o.sport. 1), 5'- GACTCTAGCC TAGGCTTTTG C-3 (SEQ ID NO:16) for amplification of the 5'-region from a pCMV. SPORT human leukocyte cDNA library (Life Technologies, Gaithersburg, Md.). PCR fragments generated that were >400 bp were inserted into the pGEM-T vector (Promega, Madison, Wis.) for further analysis. Restriction mapping and DNA sequence analysis showed one of the clones, pCDS2.H7, to be homologous to the N-terminal coding region of hCDS1.

To assemble the putative full-length human CDS cDNA clone, the 420 bp Acc65 I-Nde I fragment from pCDS2.H7 and the 1200 bp Nde I-Xba I fragment from clone ID#663789 were isolated. These two fragments were inserted into a Acc65 I and Xba I digested vector pbluescript SK(-)II vector via a three-part ligation to generate pSK.CDS2.

FIGS. 8A and 8B show the DNA sequence ID of the hCDS2. The nucleotide sequence analysis and restriction mapping of the cDNA clone revealed a 5'-untranslated region of 24 bp, an open reading frame capable of encoding a 445 amino acid polypeptide that spans nucleotide positions 25 to 1362 and a 3'-untranslated region of 1126 bp. The ATG initiation site for translation was localized at nucleotide positions 25–27 and fulfilled the requirement for an adequate initiation site according to Kozak (Kozak, Critical Rev. Biochem. Mol. Biol. 27:385–402, 1992).

Amino acid sequence alignment of the hCDS2 coding sequence with the human CDS1 shows 64% identity (FIG. 9). The amino acids that are identical between the two sequences are highlighted.

Expression of Human CDS cDNA in Mammalian Cells hCDS1

To see if overexpression of hCDS1 would have any effect on mammalian cells, the entire cDNA insert (~2,000 base pairs) from pSK.hcds was cleaved with Asp718 I and Not I for insertion into the mammalian expression vector pCE2 to generate pCE2.hCDS. The plasmid pCE2 was derived from pREP7b (Leung et al. Proc. Natl. Acad. Sci. USA, 92:4813–4817, 1995) with the RSV promoter region replaced by the CMV enhancer and the elongation factor-1α (EF-1α) promoter and intron. The CMV enhancer came from a 380 base pair Xha I-Sph I fragment produced by PCR from pCEP4 (Invitrogen, San Diego, Calif.) using the primers 5'-GGCTCTAGAT ATTAATAGTA ATCAATTAC-3' (SEQ ID NO. 7) and 5'-CCTCACGCAT GCACCATGGT AATAGC-3' (SEQ ID NO. 8). The EF-1α promoter and intron (Uetsuki et al., J. Biol. Chem., 264:5791–5798, 1989) came from a 1200 base pair Sph I-Asp718 I fragment produced by PCR from human genomic DNA using the primers 5'-GGTGCATGCG TGAGGCTCCG GTGC-3' (SEQ ID NO. 9) and 5'-GTAGTTTTCA CGGTACCTGA AATGGAAG-3' (SEQ ID NO. 10). These 2 fragments were ligated into a Xba I/Asp7 18 I digested vector derived from pREP7b to generate pCE2.

A second clone, pCE2.hCDS2, was constructed that lacked the human CDS 3'-UT region (520 nt). An Asp7l8 I (in the multiple cloning site)/NcoI fragment and a NcoI/BaamHI fragment from pSK.hCDS were combined in a three-part ligation with Asp718 I/BamHI digested pCE2. Northern blot analysis of 293-EBNA human embryonic kidney cells transiently transfected with CDS cDNA expression plasmids (pCE2.hCDS or pCE2.hCDS2) showed that deletion of the entire 3'-UT region had little effect on CDS steady-state mRNA levels.

The CDS activity in transfected cell fractions (membranes, cytosol, nuclei/unbroken cells) was determined by incorporation of (α-$^{32}$P)CTP into ($^{32}$P)CDP-DAG in the presence of exogenously added PA substrate. Cells were fractionated by resuspending previously frozen cell pellets in cold hypotonic lysis buffer (HLB; 10 mM KCl, 1.5 mM MgCl$_2$, 10 mM Tris, pH 7.4, 2 mM benzamidine HCl, and 10 µg/ml each leupeptin, soybean trypsin inhibitor, and pepstatin A) at approx. 5×10$^7$ cells/ml. After 10 min. on ice, cells were dounced (Wheaton pestle A) 40 strokes, then spun 500×g, 10 min. at 4° C. to remove nuclei and unbroken cells. The resuspension of the pellet, incubation, and low speed spin were repeated twice. The final "nuclei/unbroken cells" pellet was resuspended in 50–100 µl HLB. Supernatants were spun at 109,000×g, 30 min. at 4° C. generating "cytosol" supernates and "membrane" pellets. The pellets were resuspended in 150–225 µl HLB. An aliquot of each fraction was removed for determination of protein concentration by a BCA assay. Fractions were stored at −70° C. All assays were done on fractions after one thaw.

The in vitro CDS activity assay conditions were a modification of methods described previously (Mok et al., FEBS Letters 312:236–240,1992; and Wu et al., Nature 373:216–222,1995). Briefly, each 0.3 ml reaction combined 0.23 mM PA (Sigma; from egg yolk lecithin), 50 mM Tris-maleate, pH 7.0, 1.5% Triton X-100, 0.5 mM DTT, 75–500 µg protein from cell fractions, 30 mM $MgCl_2$, and 2 µCi ($\alpha$-$^{32}$P)CTP. $MgCl_2$ and ($\alpha$-$^{32}$P)CTP were added just prior to a 10 min. incubation at 37° C. The reactions were terminated with 4 ml chloroform:methanol (1:1) and vortexing. The organic phase was extracted three times with 1.8 ml 0.1N HCl with 1 M NaCl, and vortexing. Radioactivity in the organic phase was determined by scintillation counting or TLC.

A flip-flop TLC (ffTLC) system (Gruchalla et al., *J. Immunol.* 144:2334–2342, 1990) was modified for the separation of CDP-DAG and PA. Specifically, 200 ml of organic phase was dried and brought up in 20 µL $CHCl_3$:MeOH (2:1) and spotted in the center of a 20×20 cm TLC plate (Analtech Silica Gel HP-HLF). TLC was run in $CHCl_3$:MeOH:$NH_4OH$:$H_2O$ (65:30:4:1) until the solvent had reached the top of the plate. In this solvent system, neutral and cationic lipids migrate, whereas PA, CDP-DAG and other anionic lipids stay near the origin. The plate was dried and visualized by UV with 0.05% primulin stain (Sigma, St. Louis, Mo.) in 80% acetone. The plate was cut below the PC standard, and the bottom half of the plate was rotated 1800 and run in $CHCl_3$:MeOH:Acetic Acid:$H_2O$ (80:25:15:5) to enable migration of the anionic lipids until the solvent reached the top of the plate. The radioactive bands on the TLC plate were quantified using a STORM® phosphorimager (Molecular Dynamics, Sunnyvale, Calif.). Non-radiolabeled lipid standards were stained with primulin and visualized by fluorescence using the STORM®.

FIG. 5 shows the results of in vitro CDS activity assays on cell fractions from stable transfectants of NCl-H460 cells. CDS activity was assessed by conversion of ($\alpha$-$^{32}$P)CTP to ($^{32}$P)CDP-DAG in in vitro reactions that required addition of an exogenous PA substrate. This is a representative histogram comparing the radiolabel incorporated into various cell fractions (membranes, cytosol, and nuclei/unbroken cells) from NCl-H460 cells stably transfected with the hCDS1 cDNA (pCE2.hCDS) or vector only (pCE2). In all fractions, the CDS cDNA increased radiolabel in the organic phase of the reactions. Total CDS activity was much greater in membrane fractions, as would be expected for membrane associated CDS, compared to cytosol fractions. Activity in unbroken cells masked the activity specific to nuclei.

FIG. 6 is a representative phosphorimage of [$^{32}$p] phospholipids from membrane fraction CDS assay reactions after the second dimension of ffTLC. FIG. 6 confirms that the radiolabeled product found in the membrane fractions does migrate with a CDP-DAG standard on TLC. The identities of labeled bands were determined by migration of phospholipid standards visualized by UV or FL imaging on the STORM after primulin staining. Lanes 1–3 represent triplicate samples derived from membranes of NCl-H460 cells transfected with the hCDS1 expression vector, and lanes 4–6 represent triplicate samples from transfectants with the control vector. Cells transfected with the hCDS1 cDNA showed 1.6–2.4 fold more CD S activity in membrane fractions than vector transfectants. The relative CDS activity between CDS transfectants and vector transfectants was similar when determined by scintillation counting or TLC analysis. Similar CDS activity was seen in two different transfected human cell lines, NCl-H460 and BCV304. The average specific activity of CDS in membranes of CDS transfectants was 2.7 fmol/min/mg protein compared to 1.4 fmol/min/mg protein in membranes of vector transfectants. These results demonstrated that overexpression of the human CDS cDNA clone lead to an increase in CDS activity in cell fractions and that activity in an in vitro assay was completely dependent on the addition of PA. These data indicate that the human cDNA clone of SEQ ID NO. 1 does encode CDS activity.

hCDS2

To see if overexpression of hCDS2 has an effect in mammalian cells, the entire cDNA insert (~1,900 bp) from pSK.CDS2 was cleaved with Asp718 I and Xba I for insertion into a mammalian inducible expression vector pIND (Invitrogen, San Diego, Calif.) to generate pI__CDS2.

pI__CDS2 DNA and pVgRXR (Invitrogen, San Diego, Calif.) DNA were co-transfected into ECV304 cells (American Type Culture Collection, Rockville, Md.) with a Cell-Porator™ (Life Technologies, Gaithersburg, Md.) using conditions described previously (Cachianes, et al., *Biotechniques* 15:255–259, 1993). After adherence of the transfected cells 24 hours later, the cells were grown in the presence of 500 µg/ml G418 (Life Technologies, Gaithersburg, Md.) and 100 µg/ml Zeocin (Invitrogen, San Diego, Calif.) to select for cells that had incorporated both plasmids. G418 and Zeocin resistant clones that expressed CDS2 mRNA at a level more than 10 fold higher in the presence of muristerone A (Invitrogen, San Diego, Calif.) relative to uninduced or untranfected cells based on Northern Blot analysis (Kroczek, et al., *Anal. Biochem.* 184: 90–95, 1990) were selected for further study.

The CDS activity in ECV304 cells transfected with pI__CDS2 DNA and pVgRXR DNA with or without muristerone A induction was compared using a TLC assay (Weeks et al, *DNA Cell Biol.* 16: 281–289, 1997).

FIG. 10 shows an example of hCDS2 assay results by measuring the production of [32P]CDP-DAG after TLC analysis. The identities of labeled bands were determined based on Rf values obtained for standard phospholipids visualized by primulin staining. The left two bars represent triplicate samples derived from ECV304 cells transfected with pVgRXR and the control vector pIND in the absence or presence of the inducer muristerone A. The enzyme activity found here represents endogenous CDS activity found in ECV304 cells, as cells without or with muristerone A treatment produced similar activity. The right two bars represent triplicate samples derived from ECV304 cells transfected with pVgRXR and the inducible CDS2 vector pI__CDS2 in the absence or presence of the inducer muristerone A. Quantitation of the radioactive bands corresponding to CDP-DAG shows cells transfected with the inducible hCDS2 expression plasmid have an approximately two fold increase in activity after induction with muristerone A compared to same cells without induction or to vector control cells either with or without induction, showing that the hCDS2 cDNA clone encode a protein having CDS activity.

Complementation of Yeast cds1 Mutant with hCDS1

As the yeast CDS gene is essential for growth (Shen et al., *J. Biol Chem.* 271:789–795, 1996), another way to show that the cDNA does encode CDS activity was to determine if the human CDS cDNA will complement the growth defect of a mutant yeast strain with a deletion in the endogenous yeast CDS gene. Accordingly, the hCDS1 cDNA was cloned downstream of a GAL1 promoter in a yeast expression vector. Specifically, a Hind III-Sac I fragment from pSK.hCDS was inserted into pYES.LEU vector to generate pYES.hCDS. pYES.LEU was derived from pYES2 (Invitrogen, San Diego, Calif.) by inserting a BspH I fragment containing a LEU2 marker from pRS315 (Sikorski et al., *Genetics* 122:19–27, 1989) into the Nco I of pYES2. pYES.hCDS was introduced into a null cds1 strain of yeast, YSD90A (Shen et al., *J. Biol. Chem.* 271:789–795, 1996), with a covering plasmid, pSDG1, carrying the functional yeast CDS1. The latter plasmid was cured from cells by growth in media lacking leucine but containing uracil and galactose. PCR analysis confirmed the absence of the yeast CDS1 gene and Northern blot analysis verified expression of the hCDS1 cDNA. This strain was found to be absolutely dependent on galactose for growth. Galactose activates the GAL1 promoter for the production of human CDS protein. When the carbon source was switched to glucose, which would shut down the GAL1 promoter, growth stopped completely in less than a generation. These data show the human CDS was able to complement the growth defect of a yeast cdsi mutant.

The cells grown on galactose were lysed and assayed for CDS activity according to the assay method described (Shen et al., *J. Biol. Chem.* 271:789–795, 1996). The specific activity using yeast conditions showed activity at 20% of single copy CDS1 wild type activity. This is consistent with the above plasmid in a wild type background showing approximately 1.3 fold increase in activity when grown on galactose versus glucose.

The following experiment found that hCDS1 over-expression enhanced cytokine induced signaling in cells. Over-expression of CDS was expected to alter the cellular level of various lipid second messengers such as PA, $IP_3$ and DAG (Kent, *Anal. Rev. Biochem.* 64:315–343, 1995) and hence modulates cytokine induced signaling response in cells. To test this hypothesis, a hCDS1 expression plasmid (pCE2.hCDS), or vector (pCE2) were stably transfected into ECV304 cells (American Type Culture Collection, Rockville, Md.), an endothelial cell line that produces IL-6 and TNF-α upon stimulation with IL-1β. FIGS. 7A and 7B show that the secretion of TNF-α IL-6 in ECV304 cells stably transfected with CDS expression vector increased by >5 fold relative to ECV304 cells stably transfected with control vector after stimulation with 1 ng/ml IL-1β. However, there was little effect on the basal level of cytokine release, suggesting that over-expression of CDS amplified the cytokine signaling response, as opposed to enhancing the steady-state, basal signal, in these cells.

Expression of hCDS1 and hCDS2 mRNA in Cancer Versus Normal Prostate Tissue

Figure 11:
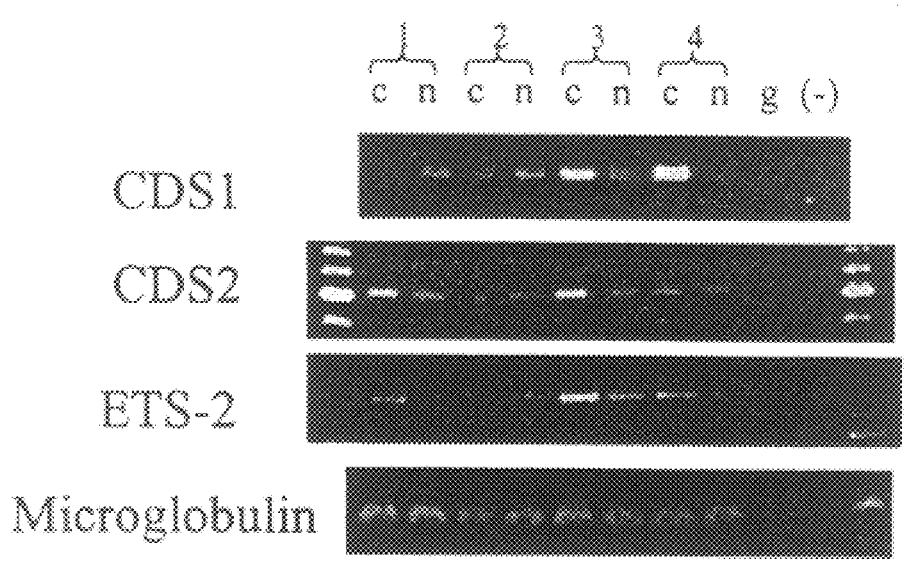
FIG. 11 shows expression of hCDS1 and hCDS2 mRNAs in cancer versus normal prostate tissues.

To examine if CDS mRNA expression in cancer versus normal tissues, RT-PCR was performed on specimens of prostate cancer tissues and the corresponding normal prostate tissues in the surgical margins from four independent patients. FIG. 11 shows hCDS1 mRNA was elevated in prostate cancer in 2 out of 4 patients, whereas hCDS2 mRNA was elevated in prostate cancer in 3 out of 4 patients. A housekeeping gene β2-microglobulin mRNA level was found to be similar in normal and cancer prostate tissues. ETS-2, a transcription factor reported to be elevated in prostate cancer (Liu et al., *Prostate* 30: 145–153, 1997), was found to be elevated in the same 3 out of 4 patients examined here, suggesting hCDS2, like ETS-2, may be a target for drug intervention in cancer therapy.

CDS Polypeptide Synthesis

Polypeptides of the present invention can be synthesized by such commonly used methods as t-BOC or FMOC protection of alpha-amino groups. Both methods involve step-wise syntheses whereby a single amino acid is added at each step starting from the C-terminus of the peptide (Coligan et al., *Current Protocols in Immunology*, Wiley Interscience, Unit 9, 1991). In addition, polypeptides of the present invention can also be synthesized by solid phase synthesis methods (e.g., Merrifield, *J. Am. Chem. Soc.* 85:2149, 1962; and Steward and Young, *Solid Phase Peptide Synthesis*, Freeman, San Francisco pp. 27–62, 1969) using copolyol (styrene-divinylbenzene) containing 0.1–1.0 mM amines/g polymer. On completion of chemical synthesis, the polypeptides can be deprotected and cleaved from the polymer by treatment with liquid HF 10% anisole for about 15–60 min at 0° C. After evaporation of the reagents, the peptides are extracted from the polymer with 1% acetic acid solution, which is then lyophilized to yield crude material. This can normally be purified by such techniques as gel filtration of Sephadex G-15 using 5% acetic acid as a solvent. Lyophilization of appropriate fractions of the column will yield a homogeneous polypeptide or polypeptide derivatives, which are characterized by such standard techniques as amino acid analysis, thin layer chromatography, high performance liquid chromatography, ultraviolet absorption spectroscopsy, molar rotation, solubility and quantitated by solid phase Edman degradation.

CDS Polynucleotides

The invention also provides polynucleotides which encode the CDS polypeptide of the invention. As used herein, "polynucleotide" refers to a polymer of deoxyribonucleotides or ribonucleotides in the form of a separate fragment or as a component of a larger construct. DNA encoding the polypeptide of the invention can be assembled from cDNA fragments or from oligonucleotides which provide a synthetic gene which is capable of being expressed in a recombinant transcriptional unit. Polynucleotide sequences of the invention include DNA, RNA and cDNA sequences. Preferably, the nucleotide sequence encoding CDS is the sequence of SEQ ID NO. 1 or of FIGS. 8A and 8B. DNA sequences of the present invention can be obtained by several methods. For example, the DNA can be isolated using hybridization procedures which are known in the art. Such hybridization procedures include, for example, hybridization of probes to genomic or cDNA libraries to detect shared nucleotide sequences, antibody screening of expression libraries to detect common antigenic epitopes or shared structural features and synthesis by the polymerase chain reaction (PCR). Such hybridization includes hybridization under high stringency conditions as described above.

Hybridization procedures are useful for screening recombinant clones by using labeled mixed synthetic oligonucleotides probes, wherein each probe is potentially the complete complement of a specific DNA sequence in a hybridization sample which includes a heterogeneous mixture of denatured double-stranded DNA. For such screening, hybridization is preferably performed on either single-stranded DNA or denatured double-stranded DNA. Hybridization is particularly useful for detection of cDNA clones derived from sources where an extremely low amount of mRNA sequences relating to the polypeptide of interest are present. Using stringent hybridization conditions to avoid non-specific binding, it is possible to allow an autoradiographic visualization of a specific genomic DNA or cDNA clone by the hybridization of the target DNA to a radiolabeled probe, which is its complement (Wallace et al. *Nucl. Acid Res.* 9:879, 1981). Specific DNA sequences encoding CDS can also be obtained by isolation and cloning of double-stranded DNA sequences from the genomic DNA, chemical manufacture of a DNA sequence to provide the necessary codons for the complete polypeptide of interest or portions of the sequence for use in PCR to obtain the complete sequence, and in vitro synthesis of a double-stranded DNA sequence by reverse transcription of mRNA isolated from a eukaryotic donor cell. In the latter case, a double-stranded DNA complement of mRNA is eventually formed which is generally referred to as cDNA. Of these three methods for developing specific DNA sequences for use in recombinant procedures, the isolation of cDNA clones is the most useful. This is especially true when it is desirable to obtain the microbial expression of mammalian polypeptides since the presence of introns in genomic DNA clones can prevent accurate expression.

The synthesis of DNA sequences is sometimes a method that is preferred when the entire sequence of amino acids residues of the desired polypeptide product is known. When the entire sequence of amino acid residues of the desired polypeptide is not known, direct synthesis of DNA sequences is not possible and it is desirable to synthesize cDNA sequences. cDNA sequence isolation can be done, for example, by formation of plasmid- or phage-carrying cDNA libraries which are derived from reverse transcription of mRNA. mRNA is abundant in donor cells that have high levels of genetic expression. In the event of lower levels of expression, PCR techniques can be used to isolate and amplify the cDNA sequence of interest. Using synthesized oligonucleotides corresponding exactly, or with some degeneracy, to known CDS amino acid or nucleotide sequences, one can use PCR to obtain and clone the sequence between the oligonucleotides. The oligonucleotide may represent invariant regions of the CDS sequence and PCR may identify sequences (isoforms) with variations from SEQ ID NO. 1 or FIGS. 8A and 8B.

A cDNA expression library, such as lambda gt 11, can be screened indirectly for the CDS polypeptide, using antibodies specific for CDS. Such antibodies can be either polyclonal or monoclonal, derived from the entire CDS protein or fragments thereof, and used to detect and isolate expressed proteins indicative of the presence of CDS cDNA.

A polynucleotide sequence can be deduced from an amino acid sequence by using the genetic code, however the degeneracy of the code must be taken into account. Polynucleotides of this invention include variant polynucleotide sequences which code for the same amino acids as a result of degeneracy in the genetic code. There are 20 natural amino acids, most of which are specified by more that one codon (a three base sequence). Therefore, as long as the amino acid sequence of CDS results in a biologically active polypeptide (at least, in the case of the sense polynucleotide strand), all degenerate nucleotide sequences are included in the invention. The polynucleotide sequence for CDS also includes sequences complementary to the polynucleotides encoding CDS (antisense sequences). Antisense nucleic acids are DNA, and RNA molecules that are complementary to at least a portion of a specific mRNA molecule (Weintraub, *Sci. Amer.* 262:40, 1990). The invention embraces all antisense polynucleotides capable of inhibiting the production of CDS polypeptide. In the cell, the antisense nucleic acids hybridize to the corresponding mRNA, forming a double-stranded molecule. The antisense nucleic acids interfere with the translation of mRNA since the cell cannot translate mRNA that is double-stranded. Antisense oligomers of about 15 nucleotides are preferred, since they are easily synthesized and are less likely to cause problems than larger molecules when introduced into the target CDS-producing cell. The use of antisense methods to inhibit translation of genes is known (e.g., Marcus-Sakura, *Anal. Biochem.* 172:289, 1988).

In addition, ribozyme nucleotide sequences for CDS are included in this invention. Ribozymes are hybrid RNA:DNA molecules possessing an ability to specifically cleave other single-stranded RNA in a manner analogous to DNA restriction endonucleases. Through the modification of nucleotide sequences which encode such RNAs, it is possible to engineer molecules that recognize specific nucleotide sequences in an RNA molecule and cleave it (Cech, *J. Amer. Med. Assn.* 260:3030, 1988). An advantage of this approach is that only mRNAs with particular sequences are inactivated because they are sequence-specific.

The CDS DNA sequence may be inserted into an appropriate recombinant expression vector. The term "recombinant expression vector" refers to a plasmid, virus or other vehicle that has been manipulated by insertion or incorporation of the genetic sequences. Such expression vectors contain a promoter sequence which facilitates efficient transcription of the inserted genetic sequence in the host. The expression vector typically contains an origin of replication, a promoter, as well as specific genes which allow phenotypic selection of the transformed cells. Vectors suitable for use in the present invention include, for example, vectors with a bacterial promoter and ribosome binding site for expression in bacteria (Gold, *Meth. Enzymol.* 185:11, 1990), expression vectors with mammalian or viral promoter and enhancer for expression in mammalian cells (Kaufman, *Meth. Enzymol.* 185:487, 1990) and baculovirus-derived vectors for expression in insect cells (Luckow et al., *J. Virol.* 67:4566, 1993). The DNA segment can be present in the vector operably linked to regulatory elements, for example, constitutive or inducible promoters (e.g., T7, metallothionein I, CMV, or polyhedren promoters).

The vector may include a phenotypically selectable marker to identify host cells which contain the expression vector. Examples of markers typically used in prokaryotic expression vectors include antibiotic resistance genes for ampicillin (β-lactamases), tetracycline and chloramphenicol (chloramphenicol acetyltransferase). Examples of such markers typically used in mammalian expression vectors include the gene for adenosine deaminase (ADA), aminoglycoside phosphotransferase (neo, G418), dihydrofolate reductase (DHFR), hygromycin-B-phosphotransferase (HPH), thymidine kinase (TK), and xanthine guanine phosphoriboseyltransferase (XGPRT, gpt).

In another preferred embodiment, the expression system used is one driven by the baculovirus polyhedrin promoter. The gene encoding the polypeptide can be manipulated by standard techniques in order to facilitate cloning into the baculovirus vector. A preferred baculovirus vector is the pBlueBac vector (Invitrogen, Sorrento, Calif.). The vector carrying the gene for the polypeptide is transfected into *Spodoptera frugiperda* (Sf9) cells by standard protocols, and the cells are cultured and processed to produce the recombinant polypeptide. See Summers et al., *A Manual for Methods of Baculovirus Vectors and Insect Cell Culture Procedures*, Texas Agricultural Experimental Station.

Once the entire coding sequence of the gene for the polypeptides has been determined, the gene can be expressed in any number of different recombinant DNA expression systems to generate large amounts of polypeptide. Included within the present invention are polypeptides having native glycosylation sequences, and deglycosylated or unglycosylated polypeptides prepared by the methods described below. Examples of expression systems known to the skilled practitioner in the art include bacteria such as *E. coli*, yeast such as Pichiapastoris, baculovirus, and mammalian expression systems such as in COS or CHO cells.

The gene or gene fragment encoding the desired polypeptide can be inserted into an expression vector by standard subcloning techniques. In a preferred embodiment, an *E. coli* expression vector is used which produces the recombinant protein as a fusion protein, allowing rapid affinity purification of the protein. Examples of such fusion protein expression systems are the glutathione S-transferase system (Pharmacia, Piscataway, N.J.), the maltose binding protein system (NEB, Beverley, Mass.), the thiofusion system (Invotrogen, San Diego, Calif.), the FLAG system (IBI, New Haven, Conn.), and the 6xHis system (Qiagen, Chatsworth, Calif.). Some of these systems produce recombinant polypeptides bearing only a small number of additional amino acids, which are unlikely to affect the CDS activity of the recombinant polypeptide. For example, both the FLAG system and the 6xHis system add only short sequences, both of which are known to be poorly antigenic and which do not adversely affect folding of the polypeptide to its native conformation. Other fusion systems produce proteins where it is desirable to excise the fusion partner from the desired protein. In a preferred embodiment, the fusion partner is linked to the recombinant polypeptide by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.) or enterokinase (Invotrogen, San Diego, Calif.).

Production of Polypeptides

Polynucleotide sequences encoding CDS polypeptides of the invention can be expressed in either prokaryotes or eukaryotes. Hosts can include microbial (bacterial), yeast, insect and mammalian organisms. Methods of expressing DNA sequences inserted downstream of prokaryotic or viral regulatory sequences in prokaryotes are known in the art (Makrides, *Microbio. Rev.* 60:512, 1996). Biologically functional viral and plasmid DNA vectors capable of expression and replication in a eukaryotic host are known in the art (Cachianes, *Biotechniques* 15:255, 1993). Such vectors are used to incorporate DNA sequences of the invention. DNA sequences encoding the inventive polypeptides can be expressed in vitro by DNA transfer into a suitable host using known methods of transfection.

Sequences encoding CDS polypeptides may be inserted into a recombinant expression vector. The term "recombinant expression vector" refers to a plasmid, virus or other vehicle that has been manipulated by inserting or incorporating genetic sequences. Such expression vectors contain a promoter sequence which facilitates efficient transcription of the inserted genetic sequence of the host. The expression vector typically contains an origin of replication and a promoter, as well as specific genes which allow phenotypic selection of the transformed cells. The DNA segment can be present in the vector, operably linked to regulatory elements, for example, a promoter (e.g., T7, metallothionein I, or polyhedren promoters). Vectors suitable for use in the present invention include, for example, bacterial expression vectors, with bacterial promoter and ribosome binding sites, for expression in bacteria (Gold, *Meth. Enzymol* 185:11, 1990), expression vector with animal promoter and enhancer for expression in mammalian cells (Kaufman, *Meth. Enzymol.* 185:487, 1990) and baculovirus-derived vectors for expression in insect cells (Luckow et al., *J. Virol.* 67:4566, 1993).

The vector may include a phenotypically selectable marker to identify host cells which contain the expression vector. Examples of markers typically used in prokaryotic expression vectors include antibiotic resistance genes for ampicillin (β-lactamases), tetracycline and chloramphenicol (chloramphenicol acetyltransferase). Examples of such markers typically used in mammalian expression vectors include the. gene for adenosine deaminase (ADA), aminoglycoside phosphotransferase (neo, G418), dihydrofolate reductase (DHFR), hygromycin-B-phosphotransferase (HPH), thymidine kinase (TK), and xanthine guanine phosphoriboseyltransferase (XGPRT, gpt).

In another preferred embodiment, the expression system used is one driven by the baculovirus polyhedrin promoter. The polynucleotide encoding CDS can be manipulated by standard techniques in order to facilitate cloning into the baculovirus vector. See Ausubel et al., supra. A preferred baculovirus vector is the pBlueBac vector (Invitrogen, Sorrento, Calif.). The vector carrying a polynucleotide encoding CDS is transfected into *Spodoptera frugiperda* (Sf9) cells by standard protocols, and the cells are cultured and processed to produce the recombinant polypeptide. See Summers et al., *A Manual for Methods of Baculovirus Vectors and Insect Cell Culture Procedures*, Texas Agricultural Experimental Station.

The polynucleotides of the present invention can be expressed in any number of different recombinant DNA expression systems to generate large amounts of polypeptide. Included within the present invention are CDS polypeptides having native glycosylation sequences, and deglycosylated or unglycosylated polypeptides prepared by the methods described below. Examples of expression systems known to the skilled practitioner in the art include bacteria such as *E. coli*, yeast such as *Pichia pastoris*, baculovirus, and mammalian expression systems such as in Cos or CHO cells.

The polynucleotides of the present invention can be inserted into an expression vector by standard subcloning techniques. In a preferred embodiment, an *E. coil* expression vector is used which produces the recombinant protein as a fusion protein, allowing rapid affinity purification of the protein. Examples of such fusion protein expression systems are the glutathione S-transferase system (Pharmacia, Piscataway, N.J.), the maltose binding protein system (NEB, Beverley, Mass.), the thiofusion system (Invitrogen, San Diego, Calif.), the Strep-tag II system (Genosys, Woodlands, Tex.), the FLAG system (IBI, New Haven, Conn.), and the 6xHis system (Qiagen, Chatsworth, Calif.). Some of these systems produce recombinant polypeptides bearing only a small number of additional amino acids, which are unlikely to affect the CDS ability of the recombinant polypeptide. For example, both the FLAG system and the 6xHis system add only short sequences, both of which are known to be poorly antigenic and which do not adversely affect folding of the polypeptide to its native conformation. Other fusion systems produce proteins where it is desirable to excise the fusion partner from the desired protein. In a preferred embodiment, the fusion partner is linked to the recombinant polypeptide by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.) or enterokinase (Invitrogen, San Diego, Calif.).

In an embodiment of the present invention, the polynucleotides encoding CDS are analyzed to detect putative transmembrane sequences. Such sequences are typically very hydrophobic and are readily detected by the use of standard sequence analysis software, such as MacDNASIS (Hitachi, San Bruno, Calif.). The presence of transmembrane sequences is often deleterious when a recombinant protein is synthesized in many expression systems, especially in *E.* coli, as it leads to the production of insoluble aggregates which are difficult to renature into the native conformation of the polypeptide.

Accordingly, deletion of one or more of the transmembrane sequences may be desirable. Deletion of transmembrane sequences typically does not significantly alter the conformation or activity of the remaining polypeptide structure. However, one can determine whether deletion of one or more of the transmembrane sequences has effected the biological activity of the CDS protein by, for example, assaying the activity of the CDS protein containing one or more deleted sequences and comparing this activity to that of unmodified CDS. Examples of assays for CDS activity are described above.

Moreover, transmembrane sequences, being by definition embedded within a membrane, are inaccessible as antigenic determinants to a host immune system. Antibodies to these sequences will not, therefore, provide immunity to the host and, hence, little is lost in terms of generating monoclonal or polyclonal antibodies by omitting such sequences from the recombinant polypeptides of the invention. Deletion of transmembrane-encoding sequences from the polynucleotide used for expression can be achieved by standard techniques. See Ausubel et al., supra, Chapter 8. For example, fortuitously-placed restriction enzyme sites can be used to excise the desired gene fragment, or the PCR can be used to amplify only the desired part of the gene.

Transformation of a host cell with recombinant DNA may be carried out by conventional techniques. When the host is prokaryotic, such as *E. coli*, competent cells which are capable of DNA uptake can be prepared from cells harvested after exponential growth phases and subsequently treated by a $CaCl_2$ method using standard procedures. Alternatively, $MgCl_2$ or RbCl can be used. Transformation can also be performed after forming a protoplast of the host cell or by electroporation.

When the host is a eukaryote, methods of transfection of DNA, such as calcium phosphate co-precipitates, conventional mechanical procedures, (e.g., microinjection), electroporation, liposome-encased plasmids, or virus vectors may be used. Eukaryotic cells can also be cotransformed with DNA sequences encoding CDS polypeptides of the present invention, and a second foreign DNA molecule encoding a selectable phenotype, such as the herpes simplex thymidine kinase gene. Another method uses a eukaryotic viral vector, such as simian virus 40 (SV40) or bovine papilloma virus to transiently infect or transform eukaryotic cells and express the CDS polypeptides.

Expression vectors that are suitable for production of CDS polypeptides preferably contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence. CDS polypeptides of the present invention preferably are expressed in eukaryotic cells, such as mammalian, insect and yeast cells. Mammalian cells are especially preferred eukaryotic hosts because mammalian cells provide suitable post-translational modifications such as glycosylation. Examples of mammalian host cells include Chinese hamster ovary cells (CHO-K1; ATCC CCL61), rat pituitary cells ($GH_1$; ATCC CCL82), HeLa S3 cells (ATCC CCL2.2), rat hepatoma cells (H-4-II-E; ATCC CRL1548) SV40-transformed monkey kidney cells (COS-1; ATCC CRL 1650) and murine embryonic cells (NIH-3T3; ATCC CRL 1658). For a mammalian host, the transcriptional and translational regulatory signals may be derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Transcriptional regulatory sequences include a promoter region sufficient to direct the initiation of RNA synthesis. Suitable eukaryotic promoters include the promoter of the mouse metallothionein I gene (Hamer et al., *J. Molec. AppL. Genet.* 1:273,1982), the TK promoter of Herpes virus (McKnight, *Cell* 31: 355, 1982); the SV40 early promoter (Benoist et al., *Nature* 290:304, 1981); the Rous sarcoma virus promoter (Gorman et aL, *Proc. Nat'l. Acad Sci. USA* 79:6777, 1982); and the cytomegalovirus promoter (Foecking et al, *Gene* 45:101, 1980). Alternatively, a prokaryotic promoter, such as the bacteriophage T3 RNA polymerase promoter, can be used to control fusion gene expression if the prokaryotic promoter is regulated by a eukaryotic promoter (Zoo et al., *Mol. Cell. Biol.* 10:4529, 1990; Kaufman et al., *Nucl. Acids Res.* 19:4485, 1991).

An expression vector can be introduced into host cells using a variety of techniques including calcium phosphate transfection, liposome-mediated transfection, electroporation, and the like. Preferably, transfected cells are selected and propagated wherein the expression vector is stably integrated in the host cell genome to produce stable transformants. Techniques for introducing vectors into eukaryotic cells and techniques for selecting stable transformants using a dominant selectable marker are described, for example, by Ausubel and by Murray (ed.), *Gene Transfer and Expression Protocols* (Humana Press 1991). Examples of mammalian host cells include COS, BHK, 293 and CHO cells.

Purification of Recombinant Polypeptides.

The polypeptide expressed in recombinant DNA expression systems can be obtained in large amounts and tested for biological activity. The recombinant bacterial cells, for example *E. coli*, are grown in any of a number of suitable media, for example LB, and the expression of the recombinant polypeptide induced by adding IPTG to the media or switching incubation to a higher temperature. After culturing the bacteria for a further period of between 2 and 24 hours, the cells are collected by centrifugation and washed to remove residual media. The bacterial cells are then lysed, for example, by disruption in a cell homogenizer and centrifuged to separate the dense inclusion bodies and cell membranes from the soluble cell components. This centrifugation can be performed under conditions whereby the dense inclusion bodies are selectively enriched by incorporation of sugars such as sucrose into the buffer and centrifugation at a selective speed. If the recombinant polypeptide is expressed in the inclusion, these can be washed in any of several solutions to remove some of the contaminating host proteins, then solubilized in solutions containing high concentrations of urea (e.g., 8 M) or chaotropic agents such as guanidine hydrochloride in the presence of reducing agents such as β-mercaptoethanol or DTT (dithiothreitol). At this stage it may be advantageous to incubate the polypeptide for several hours under conditions suitable for the polypeptide to undergo a refolding process into a conformation which more closely resembles that of the native polypeptide. Such conditions generally include low polypeptide (concentrations less than 500 mg/ml), low levels of reducing agent, concentrations of urea less than 2 M and often the presence of reagents such as a mixture of reduced and oxidized glutathione which facilitate the interchange of disulphide bonds within the protein molecule. The refolding process can be monitored, for example, by SDS-PAGE or with antibodies which are specific for the native molecule. Following refolding, the polypeptide can then be purified further and separated from the refolding mixture by chromatography on any of several supports including ion exchange resins, gel permeation resins or on a variety of affinity columns.

Isolation and purification of host cell expressed polypeptide, or fragments thereof may be carried out by conventional means including, but not limited to, preparative chromatography and immunological separations involving monoclonal or polyclonal antibodies.

These polypeptides may be produced in a variety of ways, including via recombinant DNA techniques, to enable large scale production of pure, active CDS useful for screening compounds for trilineage hematopoietic and anti-inflammatory therapeutic applications, and developing antibodies for therapeutic, diagnostic and research use.

Screening Assays using CDS Polypeptides

The CDS polypeptide of the present invention is useful in a screening methodology for identifying compounds or compositions which affect cellular signaling of an inflammatory response. This method comprises incubating the CDS polypeptides or a cell transfected with cDNA encoding CDS, with a suitable substrate, for example, PA, under conditions sufficient to allow the components to interact, and then measuring the effect of the compound or composition on CDS activity. See, for example, above, and Weeks et al., *DNA Cell Biol.* 16: 281–289, 1997. The observed effect on CDS may be either inhibitory or stimulatory. Such compounds or compositions to be tested can be selected from a combinatorial chemical library or any other suitable source (Hogan, Jr., *Nat. Biotechnology* 15:328, 1997).

Peptide Sequencing of Polypeptides

Substitutional variants typically contain the exchange of one amino acid for another at one or more sites within the protein, and are designed to modulate one or more properties of the polypeptides such as stability against proteolytic cleavage. Substitutions preferably are conservative, that is, one amino acid is replaced with one of similar shape and charge. Conservative substitutions are well known in the art and include, for example, the changes of alanine to serine; arginine to lysine; asparigine to glutamine or histidine; aspartate to glutamate; cysteine to serine; glutamine to asparigine; glutamate to aspartate; glycine to proline; histidine to asparigine or glutamine, isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Insertional variants contain fusion proteins such as those used to allow rapid purification of the polypeptide and also can include hybrid polypeptides containing sequences from other proteins and polypeptides which are homologues of the inventive polypeptide. For example, an insertional variant could include portions of the amino acid sequence of the polypeptide from one species, together with portions of the homologous polypeptide from another species. Other insertional variants can include those in which additional amino acids are introduced within the coding sequence of the polypeptides. These typically are smaller insertions than the fusion proteins described above and are introduced, for example, to disrupt a protease cleavage site.

Anti-CDS Antibodies

Antibodies to human CDS protein can be obtained using the product of a CDS expression vector or synthetic peptides derived from the CDS coding sequence coupled to a carrier (Pasnett et al., *J. Biol. Chem.* 263:1728, 1988) as an antigen. The preparation of polyclonal antibodies is well-known to those of skill in the art. See, for example, Green et al., "Production of Polyclonal Antisera," in *Immunochemical Protocols* (Manson, ed.), pages 1–5 (Humana Press 1992). Alternatively, a CDS antibody of the present invention may be derived as a rodent monoclonal antibody (MAb). Rodent monoclonal antibodies to specific antigens may be obtained by methods known to those skilled in the art. See, for example, Kohler and Milstein, *Nature* 256:495, 1975, and Coligan et al. (eds.), *Current Protocols in Immunology*, 1:2.5.1–2.6.7 (John Wiley & Sons 1991). Briefly, monoclonal antibodies can be obtained by injecting mice with a composition comprising an antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1–2.7.12 and pages 2.9.1–2.9.3. Also, see Baines et al., "Purification of Immunoglobulin G (IgG)," in *Methods in Molecular Biology*, 10:79–104 Humana Press, Inc. 1992. A CDS antibody of the present invention may also be derived from a subhuman primate. General techniques for raising therapeutically useful antibodies in baboons may be found, for example, in Goldenberg et al., international patent publication No. WO 91/11465 (1991), and in Losman et al., *Int. J Cancer* 46:310, 1990.

Alternatively, a therapeutically useful CDS antibody may be derived from a "humanized" monoclonal antibody. Humanized monoclonal antibodies are produced by transferring mouse complementarity determining regions from heavy and light chain variable regions of the mouse antibody into a human antibody variable domain, and then, substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by the publication of Orlandi et al., *Proc. Nat'l. Acad Sci. USA* 86:3833, 1989. Techniques for producing humanized MAbs are described, for example, by Jones et al., *Nature* 321:522, 1986; Riechmann et al., *Nature* 332:323, 1988; Verhoeyen et al., *Science* 239:1534, 1988; Carter et al., *Proc. Nat'l Acad Sci. USA* 89:4285, 1992; Sandhu, *Crit. Rev. Biotech.* 12: 437, 1992, and Singer et al., *J. Immun.* 150:2844, 1993.

As an alternative, a CDS antibody of the present invention may be derived from human antibody fragments isolated from a combinatorial immunoglobulin library. See, for example, Barbas et al., METHODS: *A Companion to Methods in Enzymology* 2:119 1991, and Winter et al., *Ann. Rev. Immunol* 12:433, 1994. Cloning and expression vectors that are useful for producing a human imnmunoglobulin phage library can be obtained, for example, from STRATAGENE Cloning Systems (La Jolla, Calif.). In addition, a CDS antibody of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13, 1994; Lonberg et al., *Nature* 368: 856, 1994; and Taylor et al., *Int. Immun.* 6:579, 1994.

We claim:

1. An isolated polypeptide, comprising the amino acid sequence of SEQ ID NO:12 or enzymatically-active fragments thereof, wherein said polypeptide has cytidine diphosphate diacylglycerol synthase (CDS) activity.

2. The isolated polypeptide of claim 1, wherein said polypeptide comprises the amino acid sequence of SEQ ID NO:12.

3. An isolated polypeptide, comprising an amino acid sequence having 85% sequence identity to the amino acid sequence of SEQ ID NO:12, wherein said polypeptide has CDS activity.

4. An isolated polypeptide, encoded by a polynucleotide sequence that hybridizes under high stringency conditions of 5×SSC at 65° C., followed by washing in 0.1×SSC at 65° C. to the DNA sequence selected from the group consisting of:
   (i) a complete complement of the DNA sequence of SEQ ID NO:11 and
   (ii) a complete complement of a DNA sequence encoding the polypeptide of SEQ ID NO:12
wherein said polynucleotide encodes a polypeptide having CDS activity.

5. An isolated polypeptide, encoded by a polynucleotide sequence having at least 85% sequence identity to a DNA sequence selected from the group consisting of:
   (i) the DNA sequence of SEQ ID NO:11 and
   (ii) a DNA sequence encoding the polypeptide of SEQ ID NO:12
wherein said polynucleotide encodes a polypeptide having CDS activity.

6. A method for screening one or more compounds to determine whether said one or more compounds increases or decreases CDS activity, comprising:
   (a) contacting the polypeptide of claim 1 with one or more substrates for said polypeptide and with said one or more compounds; and
   (b) measuring whether the CDS activity of said polypeptide is increased or decreased by said one or more compounds.

7. The method of claim 6, wherein said one or more compounds is selected from a combinatorial chemical library.

* * * * *